US012793818B2

(12) United States Patent
Goltra

(10) Patent No.: US 12,793,818 B2
(45) Date of Patent: *Nov. 10, 2026

(54) ELECTRONIC MEDICAL RECORDS SYSTEM UTILIZING GENETIC INFORMATION

(71) Applicant: MEDICOMP SYSTEMS, INC., Chantilly, VA (US)

(72) Inventor: Peter S. Goltra, Middleburg, VA (US)

(73) Assignee: MEDICOMP SYSTEMS, INC., Herndon, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/379,563

(22) Filed: Oct. 12, 2023

(65) Prior Publication Data

US 2024/0161887 A1 May 16, 2024

Related U.S. Application Data

(63) Continuation of application No. 14/216,599, filed on Mar. 17, 2014, now Pat. No. 11,837,340.

(60) Provisional application No. 61/801,262, filed on Mar. 15, 2013.

(51) Int. Cl.

*G16H 10/60* (2018.01)
*G16B 20/00* (2019.01)
*G16B 20/20* (2019.01)
*G16B 45/00* (2019.01)
*G16B 50/00* (2019.01)
*G16B 50/30* (2019.01)

(52) U.S. Cl.

CPC ............. *G16H 10/60* (2018.01); *G16B 20/00* (2019.02); *G16B 20/20* (2019.02); *G16B 45/00* (2019.02); *G16B 50/00* (2019.02); *G16B 50/30* (2019.02)

(58) Field of Classification Search

CPC ........ G16B 45/00; G16B 50/00; G16B 20/00; G16H 10/60

USPC .............................................................. 705/2

See application file for complete search history.

(56) References Cited

U.S. PATENT DOCUMENTS 4,839,822 A 6/1989 Dormond et al.
5,089,978 A 2/1992 Lipner et al.
5,262,943 A 11/1993 Thibado et al.
5,265,010 A 11/1993 Evans-Paganelli et al.
5,387,164 A 2/1995 Brown, Jr.
5,453,009 A 9/1995 Feldman (Continued)

FOREIGN PATENT DOCUMENTS

WO WO-2004050840 A2 * 6/2004 ............. G06F 19/20
WO WO-2004090100 A2 * 10/2004 ............. G16B 45/00
WO WO-2009117122 A2 * 9/2009 ........... C12Q 1/6886

OTHER PUBLICATIONS

Hale, Paul J; Genome-wide meta-analysis of genetic susceptible genes for Type 2 Diabetes; BMC Systems Biology 6. Suppl 3: S16. BioMed Central. (2012) ; (Year: 2012).*

(Continued)

*Primary Examiner* — Hiep V Nguyen

(74) *Attorney, Agent, or Firm* — Merchant & Gould P.C.

(57) ABSTRACT

Methods, apparatuses, and systems having an electronic medical records system which intelligently selects medical findings or related information and maps them to associated genes. An electronic medical records system intelligently selects genes and maps them to associated medical findings or other related information.

15 Claims, 21 Drawing Sheets

(56) References Cited

U.S. PATENT DOCUMENTS

| | | | |
|---|---|---|---|
| 5,524,645 | A | 6/1996 | Wills |
| 5,823,949 | A | 10/1998 | Goltra |
| 6,177,940 | B1 | 1/2001 | Bond et al. |
| 7,120,646 | B2 | 10/2006 | Streepy, Jr. |
| 7,233,938 | B2 | 6/2007 | Macpherson et al. |
| 7,379,946 | B2 | 5/2008 | Carus et al. |
| 7,447,988 | B2 | 11/2008 | Ross |
| 7,610,192 | B1 | 10/2009 | Jamieson |
| 7,624,030 | B2 | 11/2009 | Feder et al. |
| 7,668,737 | B2 | 2/2010 | Streepy, Jr. |
| 7,725,330 | B2 | 5/2010 | Rao et al. |
| 7,739,123 | B1 | 6/2010 | Rappaport |
| 8,086,468 | B2 | 12/2011 | Kim |
| 9,865,025 | B2 | 1/2018 | Ragusa |
| 2002/0198885 | A1 | 12/2002 | Streepy, Jr. |
| 2003/0105638 | A1 | 6/2003 | Taira |
| 2003/0113727 | A1 | 6/2003 | Girn et al. |
| 2003/0167189 | A1 | 9/2003 | Lutgen et al. |
| 2003/0204418 | A1 | 10/2003 | Ledley |
| 2004/0078236 | A1 | 4/2004 | Stoodley et al. |
| 2004/0191788 | A1 | 9/2004 | Gleba et al. |
| 2004/0220831 | A1 | 11/2004 | Fabricant |
| 2005/0027564 | A1 | 2/2005 | Yantis |
| 2005/0027566 | A1 | 2/2005 | Haskell |
| 2005/0107672 | A1 | 5/2005 | Lipscher et al. |
| 2005/0108054 | A1 | 5/2005 | Gottlieb |
| 2005/0240439 | A1 | 10/2005 | Covit et al. |
| 2006/0031218 | A1 | 2/2006 | Cipollone |
| 2006/0101055 | A1 | 5/2006 | Valdiserri et al. |
| 2006/0122865 | A1 | 6/2006 | Preiss et al. |
| 2006/0253431 | A1 | 11/2006 | Bobick et al. |
| 2006/0257895 | A1 | 11/2006 | Pinkel et al. |
| 2007/0088559 | A1 | 4/2007 | Kim |
| 2007/0214013 | A1 | 9/2007 | Silverman |
| 2007/0244911 | A1 | 10/2007 | Dick |
| 2008/0016042 | A1 | 1/2008 | Mcknight |
| 2008/0021288 | A1 | 1/2008 | Bowman et al. |
| 2008/0046292 | A1 | 2/2008 | Truscott et al. |
| 2008/0091464 | A1 | 4/2008 | Lipscher et al. |
| 2008/0215367 | A1 | 9/2008 | Marshall |
| 2008/0215369 | A1 | 9/2008 | Lareau |
| 2008/0216010 | A1 | 9/2008 | Lareau |
| 2008/0288292 | A1 | 11/2008 | Bi et al. |
| 2008/0319942 | A1 | 12/2008 | Courdy et al. |
| 2009/0055378 | A1 | 2/2009 | Alecu et al. |
| 2009/0119128 | A1 | 5/2009 | Fitzgerald et al. |
| 2009/0210450 | A1 | 8/2009 | Goltra |
| 2009/0240522 | A1 | 9/2009 | Handal |
| 2009/0299645 | A1* | 12/2009 | Colby .................... G16B 20/10 506/7 |
| 2009/0307179 | A1 | 12/2009 | Colby et al. |
| 2009/0307181 | A1 | 12/2009 | Colby et al. |
| 2010/0017222 | A1 | 1/2010 | Yeluri et al. |
| 2010/0088117 | A1 | 4/2010 | Belden et al. |
| 2010/0094657 | A1 | 4/2010 | Stern et al. |
| 2010/0131299 | A1 | 5/2010 | Hasan et al. |
| 2010/0161354 | A1 | 6/2010 | Lim et al. |
| 2010/0179827 | A1 | 7/2010 | Mccallie, Jr. et al. |
| 2010/0274584 | A1 | 10/2010 | Kim |
| 2010/0280851 | A1 | 11/2010 | Merkin |
| 2010/0305969 | A1 | 12/2010 | Bacon |
| 2010/0318549 | A1 | 12/2010 | Mayr et al. |
| 2010/0328235 | A1 | 12/2010 | Taute |
| 2010/0331641 | A1* | 12/2010 | Bangera ............... A61B 5/0002 702/19 |
| 2011/0004628 | A1 | 1/2011 | Armstrong et al. |
| 2011/0004847 | A1 | 1/2011 | Herrold et al. |
| 2011/0098193 | A1 | 4/2011 | Kingsmore et al. |
| 2011/0225000 | A1 | 9/2011 | Selim |
| 2012/0060216 | A1 | 3/2012 | Chaudhri et al. |
| 2012/0110016 | A1 | 5/2012 | Phillips |
| 2012/0208706 | A1 | 8/2012 | Downing et al. |
| 2012/0215559 | A1 | 8/2012 | Habboush et al. |
| 2012/0239671 | A1 | 9/2012 | Chaudhri et al. |
| 2012/0290322 | A1 | 11/2012 | Bergman et al. |
| 2013/0006653 | A1 | 1/2013 | Mills |
| 2013/0046529 | A1 | 2/2013 | Grain et al. |
| 2013/0046758 | A1 | 2/2013 | Kim et al. |
| 2013/0054678 | A1 | 2/2013 | Williams et al. |
| 2013/0096943 | A1 | 4/2013 | Carey et al. |
| 2013/0218598 | A1 | 8/2013 | Aita et al. |
| 2013/0231957 | A1 | 9/2013 | Lareau |
| 2014/0006013 | A1 | 1/2014 | Markatou et al. |
| 2014/0222349 | A1 | 8/2014 | Higgins et al. |

OTHER PUBLICATIONS

Viel, Kevin Roland; Refining the roles of genetic, environmental, and endogenous factors in Factor VIII activity levels; Emory University. ProQuest Dissertations Publishing, 2007. 3298459. (Year: 2007).

Cho, I. et al., "The Human Microbiome: at the interface of health and disease," Nature Reviews Genetics, vol. 13, No. 4, pp. 260-270 (Apr. 2012).

Cooney, E., "Mapping the healthy human microbiome," Broad Institute, http://www.broadinstitute.org/news/4199, 3 pages (Jun. 13, 2012).

Dewey, F. et al., "DNA Sequencing: Clinical Applications of New DNA Sequencing Technologies," Circulation, vol. 125, No. 7, pp. 931-944 (Feb. 21, 2012).

Franca, L. et al., "A review of DNA sequencing techniques," Quarterly Reviews of Biophysics, vol. 35, No. 22, pp. 169-200 (2002).

International Search Report and Written Opinion for PCT/US2014/030653 dated Aug. 28, 2014.

Plottel, C. et al., "Microbiome and Malignancy," Cell Host & Microbe, vol. 10, No. 4, pp. 324-335 (Oct. 20, 2011).

Richardson, P., "Special Issue: Next Generation DNA Sequencing," Genes, vol. 1, No. 3, pp. 385-387 (Oct. 27, 2010).

The Economist, "Modern Medicine: Microbes maketh man," http://www.economist.com/node/21560559/print, 3 pages (Aug. 18, 2012).

The Economist, "The human microbiome: Me, myself, us," http://www.economist.com/node/21560523/print, 8 pages (Aug. 18, 2012).

The Human Microbiome Project Consortium, "A framework for human microbiome research," Nature, vol. 486, pp. 215-221 (Jun. 14, 2012).

Wallis, G., "The Genetic Basis of Human Disease," Biochemistry Across the School Curriculum, Guidance Notes for Advanced Biology No. 10, Biochemical Society, 66 pages (1999).

European Search Report for Application No. 14765205 (Date Completed Oct. 13, 2016).

"Google patents search", Sep. 15, 2016.

"Google patents search", May 7, 2018.

"Google patents search", Sep. 23, 2019.

Yan et al. "The Internet Based Knowledge Acquisition and Management Method to Construct Large Scale Distributed Medical Expert Systems", 2004, 1-10 pages.

"The ICD 10 Classification of Mental and Behavioural Disorders", 1993, World Health Organization.

European Search Report for EP14765205, dated Oct. 13, 2016.

Non-Final Office Action for U.S. Appl. No. 13/773,520, dated Jan. 4, 2022, 23 pages.

* cited by examiner

RELATIONSHIP OF DATA IN DATABASE

FIG. 9

| ALL RESULTS FOR LONG QT SYNDROME 402 | | | |
|---|---|---|---|
| DESCRIPTION 406 | CODE 408 | RS 410 | NODEKEY 412 |
| SCN5A GENE 406a | 320602 408a | 1 410a | DFGP3P21SC 412 |
| KCNQ1 GENE 406b | 321905 408b | (2) 410b | DFGP11P15KC 412 |
| KCNH2 LENE 406c | 341083 408c | (2) 410c | DFGP12 P11KC 412 |
| KCNJ2 GENE 406d | 395998 408d | O 410d | DFGP17 Q23KC 412 |
| KCNE1 GENE 406e | 311467 408e | (3) 410e | DFGP21 Q22KC 412 |

| FILTERING OF RELEVANT RESULTS FOR LONG QT SYNDROME 404 | | | |
|---|---|---|---|
| DESCRIPTION 414 | CODE 416 | RS 418 | NODEKEY 420 |
| KCNQ1 GENE 414a | 321905 416a | 2 418a | DFGP11P15KC 420a |
| KCNH2 GENE 414b | 341083 416b | 2 418b | DFGP12P11KC 420b |
| KCNE1 GENE 414c | 311467 416c | 3 418c | DFGP21Q22KC 420c |

FIG. 13

800

802

FURTHER DETAILS ON SELECTED GENE

Gene Name
- Alternative names

Approved Gene Symbol — 804
- Alternative symbols

| Cytogenetic location/ chromosomal coordinates | Disease | Disease Terms | Disease Class | Phenotype No. | Relevance Score |
|---|---|---|---|---|---|
| Gene A | Disease A | Term A | Class A | Phenotype 1 | 2 |
| Gene B | Disease B | Term B | Class B | Phenotype 2 | 1 |

Medical Findings
- Cardiovascular
- Pulmonary
- Muscoskeletal
- Neurological
- Psychological
- Risk factors
- References Genetics
- Biophysical and functional characteristics of gene/defects in gene
- Polynucleotide sequence of gene
- Genetic variants
    - Polynucleotide sequence of genetic variants
- Ideogram
- References Medical Decision Support
- Examination protocols
- Laboratory testing protocols
- Genetic testing protocols
- Case studies
- References Treatment
- Drug Therapy
    - Drugs
        - Dosage
        - Side effects
        - Contraindications
- Surgical procedures
- Radiation therapy options
    - Dosage
    - Side effects
    - Contraindications
- Case studies
- References

PATIENT:
JOHN DOE
DOB: 08-08-71

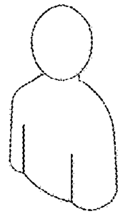

1400

| Body Site (BS) | Domain | Organism Name | Taxonomy | Disease Terms | Disease Class | Relevance Score | Internal Medical Code |
|---|---|---|---|---|---|---|---|
| Gene A and/or BS A | Domain A | Organism A | Taxonomy A | Terms A, B | Classes A, B | 2 | Code A |
| | | • • • | | | | | |
| Gene D and/or BS D | Domain B | Organism D | Taxonomy D | Term D | Classes D, E | 1 | Code D |

FIG. 20

1500

1502

FURTHER DETAILS ON SELECTED MICROBIOME GENE

Taxon Description

- Species name
  - Strain
    - Domain
      - Archaeal
      - Bacterial
      - Eukaryal
      - Virus
    - Phylum
    - Class
  - Classification
    - Order
    - Family
    - Genus
    - Specius
- Phenotype characteristics
- Prevalence and source
- Disease associations
  - Medical Findings
    - Cardiovascular
    - Pulmonary
    - Muscoskeletal
    - Neurological
    - Psychological
  - Medical Decision Support
    - Examination protocols
    - Laboratory testing protocols
    - Genetic testing protocols
    - Case Studies
    - References
  - Treatment
    - Drug Therapy
      - Drugs
      - Dosage
      - Side effects
      - Contraindications
    - Surgical procedures
    - Radiation therapy options
      - Dosage
      - Side effects
      - Contraindications
    - Case studies
    - References
- Genetic information
  - Genomic sequences
    - GeneBank ID No.
  - 16S rRNA sequence
    - GeneBank ID No.
- Testing Protocols
  - Cultivation conditions
- References

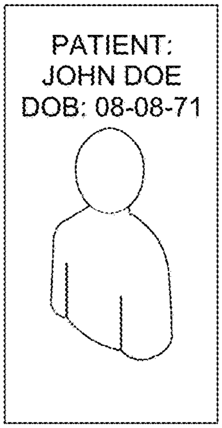

ELECTRONIC MEDICAL RECORDS SYSTEM UTILIZING GENETIC INFORMATION

CROSS-REFERENCE TO RELATED APPLICATIONS

The present application is a continuation application of U.S. application Ser. No. 14/216,599, entitled "ELECTRONIC MEDICAL RECORDS SYSTEM UTILIZING GENETIC INFORMATION," filed on Mar. 17, 2014, which claims the benefit of provisional U.S. Application No. 61/801,262, entitled "ELECTRONIC MEDICAL RECORDS SYSTEM UTILIZING GENETIC INFORMATION" and filed Mar. 15, 2013, the entire disclosures of which are expressly incorporated herein by reference.

BACKGROUND

Variant genes or genetic mutations increasingly are being identified as a basis for or a contributing factor in diseases or disorders and health issues relating to specific bodily functions. For example, certain forms of cancer have been found to arise from translocation of one or more genes or an accumulation of genetic mutations in one or more genes. Common disorders such as diabetes and obesity have also been found to have a genetic basis or component in some patients. These genes are not limited to the genome of the patient but can also include genes from microbial communities that exist throughout the human body, known as the human microbiome. Bacteria or viruses that exist within the human microbiome have been found to contribute to cardiovascular disease, malignancies, obesity, and metabolic disorders such as diabetes. Bacterial and viral genes also may be useful in identifying microorganisms in the human microbiome that are the basis for or a contributing factor to an abnormal medical finding(s). As more diseases and disorders are found to have a basis in the human microbiome or a genetic component in the human genome or metagenome of the human microbiome that is the basis for or contributes to the abnormal medical finding(s), the management of genetic information is becoming more important for the effective treatment and management of affected patients. A need therefore exists for electronic medical records systems capable of managing and utilizing genetic information in the treatment and management of patients.

SUMMARY

In general terms, this disclosure is directed to an electronic medical records system which intelligently selects medical findings or related information and maps them to associated genes. In alternate embodiments, the electronic medical records system intelligently selects genes and maps them to associated medical findings or other related information. It should be appreciated that the above-described subject matter may be implemented as a computer-controlled apparatus, a computer process, a computing system, or as an article of manufacture such as a computer-readable storage medium. This Summary is provided to introduce concepts that are embodied in the various methods, apparatuses, and systems described below in the Detailed Description. This Summary is not intended to identify key features or essential features of the claimed subject matter, nor is it intended that this Summary be used to limit the scope of the claimed subject matter. Furthermore, the claimed subject matter is not limited to implementations that solve any or all disadvantages noted in any part of this disclosure.

BRIEF DESCRIPTION OF THE DRAWINGS

FIG. 9 is a schematic diagram illustrating an exemplary embodiment of a filtering process conducted by a medical information records system.

FIG. 13 is yet another exemplary embodiment of an interactive user interface presented by the electronic healthcare system.

FIG. 20 is yet another exemplary embodiment of an interactive user interface presented by the electronic healthcare system.

DETAILED DESCRIPTION

Figure 1:
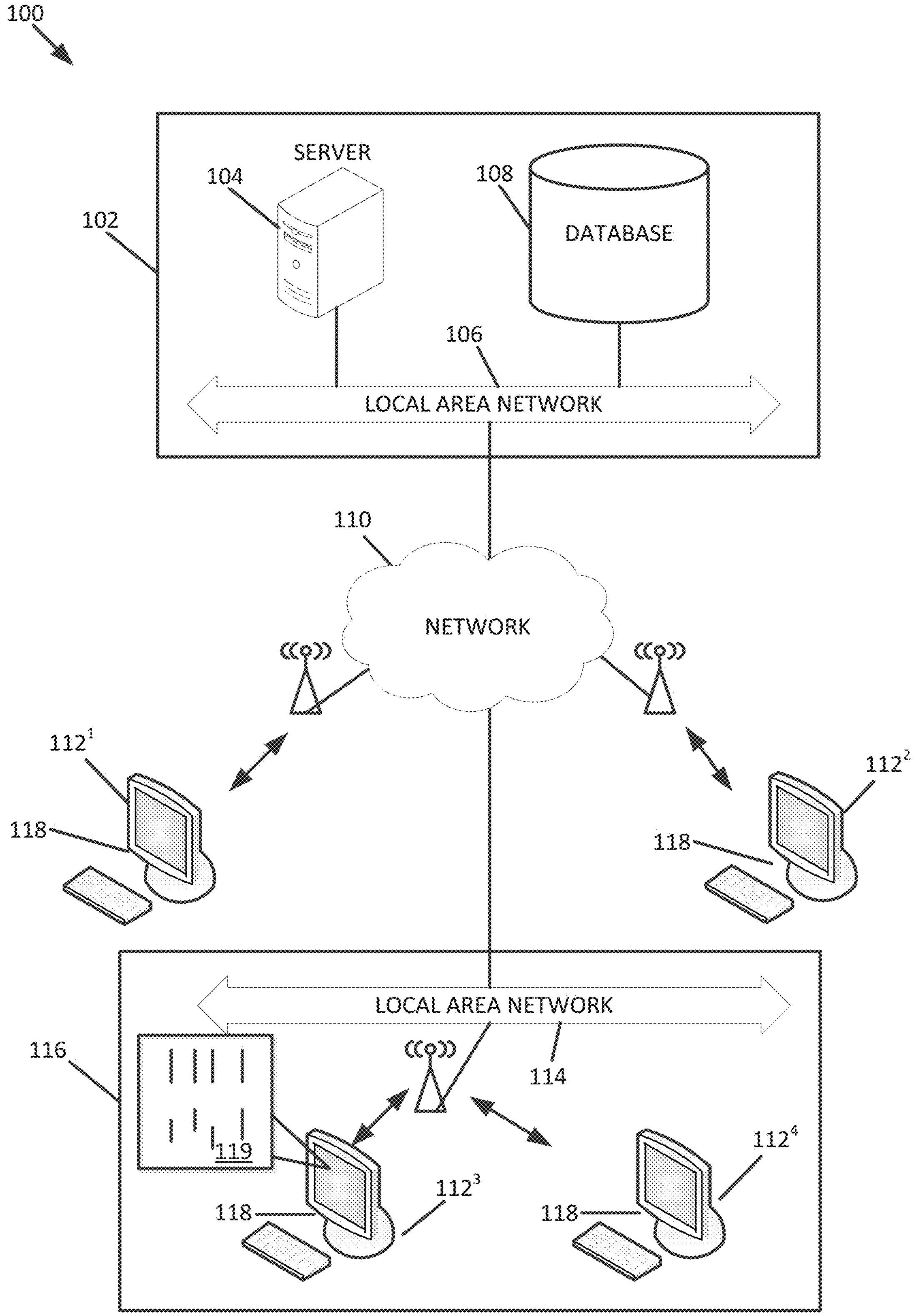
FIG. 1 illustrates an exemplary embodiment of an electronic healthcare system.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments.

In general, the present disclosure describes systems and methods involving the use and presentation of genetic information in a medical context. The below description describes systems and methods that open up new possibilities for the use and presentation of genetic information in the study and evaluation of medical findings.

A. Definitions

Whenever appropriate, terms used in the singular also will include the plural and vice versa. The use of "a" herein means "one or more" unless stated otherwise or where the use of "one or more" is clearly inappropriate. The use of "or" means "and/or" unless stated otherwise. The use of "comprise," "comprises," "comprising," "include," "includes," and "including" are interchangeable and not intended to be limiting. The terms "such as," "for example," "e.g.," and "i.e." also are not intended to be limiting. For example, the term "including" shall mean "including, but not limited to."

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "biological sample" or "patient sample" as used herein refers to samples obtained from a subject, including skin, hair, tissue, blood, plasma, serum, cells, sweat, saliva, bone, teeth, feces, tissue, biopsy samples, urine, and the like.

The terms "nucleic acid" and "polynucleotide" are used interchangeably to describe a polymer of any length, e.g., greater than about 10 bases, greater than about 100 bases, greater than about 500 bases, greater than 1000 bases, usually up to about 10,000 or more bases composed of nucleotides, such as deoxyribonucleotides or ribonucleotides, or compounds produced synthetically which can hybridize with naturally occurring nucleic acids in a sequence specific manner analogous to that of two naturally occurring nucleic acids in Watson-Crick base pairing interactions.

The term "primer" refers to a polynucleotide capable of acting as a point of initiation of synthesis along a complementary strand when conditions are suitable for synthesis of a primer extension product. The synthesizing conditions include the presence of four different nucleotide bases and at least one polymerization-inducing agent such as reverse transcriptase or DNA polymerase. The primers are present in a suitable buffer, which may include constituents which are co-factors or affect conditions such as pH and the like at various suitable temperatures. A primer is preferably a single strand sequence, such that amplification efficiency is optimized. Double stranded sequences can also be utilized. Primers are typically at least about 15 nucleotides. In embodiments, primers can have a length of anywhere from 15 to 2000 nucleotides.

The term "probe" refers to a nucleic acid that hybridizes to a target sequence. A probe can include a detectable label. Detectable labels include, but are not limited to, a fluorophore (such TexasRed®, fluorescein isothiocyanate, and the like) and a hapten, such as biotin. A detectable label can be covalently attached directly to the probe. A probe including a fluorophore also may further include a quencher, such Black Hole Quencher™, Iowa Black™, and the like.

As used herein, the term "gene" means a DNA or RNA sequence that codes for a polypeptide or RNA sequence. The term includes RNA sequences, such as ribozymes, microRNA, and small interfering RNA, that have a functional or regulatory activity in an organism. The gene may include a leader sequence preceding the coding region or a trailer sequence following the coding sequence. The gene may include a regulatory sequence or promoter sequence that regulates or promotes expression of the gene. The gene also may include intervening sequences, introns, between individual coding sequences, exons.

The chromosomal location and features of a human gene, including mutations thereof, can be described using cytogenetic notation such as the International System for Human Cytogenic Nomenclature (ISCN). See, for example, ISCN 2013: An International System for Human Cytogenetic Nomenclature (2013), Edited by Shaffer et al., 1st Ed., S. Karger, December 2012. Table 1 summarizes commonly used ISCN symbols and abbreviations that may be used in databases described herein to describe the location of human genes and chromosomes and mutations thereto.

TABLE 1

| Symbol | Description |
|---|---|
| , | Separates modal number (total number of chromosomes), sex chromosomes, and chromosome abnormalities |
| − | Loss of a chromosome |
| ( ) | Grouping for breakpoints and structurally altered chromosomes |
| + | Gain of a chromosome |
| ; | Separates rearranged chromosomes and breakpoints involving more than one chromosome |
| / | Separates cell lines or clones |
| // | Separates recipient and donor cell lines in bone marrow transplants |
| del | Deletion |
| der | Derivative chromosome |
| dic | Dicentric chromosome |
| dn | de novo (not inherited) chromosomal abnormality |
| dup | Duplication of a portion of a chromosome |
| fra | Fragile site (usually used with Fragile X syndrome) |
| h | Heterochromatic region of chromosome |
| i | Isochromosome |
| ins | Insertion |
| inv | Inversion |
| .ish | Precedes karyotype results from FISH analysis |
| mar | Marker chromosome |
| mat | Maternally-derived chromosome rearrangement |
| p | Short arm of a chromosome |
| pat | Paternally-derived chromosome rearrangement |
| psu dic | *pseudo dicentric* - only one centromere in a Dicentric chromosome is active |
| q | Long arm of a chromosome |
| r | Ring chromosome |
| t | Translocation |
| ter | Terminal end of arm (e.g. 2qter refers to the end of the long arm of chromosome 2) |
| tri | Trisomy |
| trp | Triplication of a portion of a chromosome |

As used herein, the term "variant" means a variant of a wild-type gene. Due to genetic variation, there may be multiple variants, or alleles, of a given gene. An allele refers to any of two or more alternative forms of a gene occupying a given locus of a chromosome. If two copies of the same allele are present in an individual, the individual is homozygous for that allelic form of the gene. If different alleles are present in an individual, the individual is heterozygous for that gene. As used herein, a normal variant of a gene means an allelic variant of the gene of interest that is not associated with pathogenicity and functions similarly to the gene of interest. A variant of uncertain significance means that the gene has been identified as an allelic variant of the gene of interest but the relationship of the variant gene to a pathogenicity, if any, is not yet known. A pathogenic variant means the allelic variant of the gene of interest is associated with an abnormal medical finding(s). Databases cataloging human genes and their variants are publically available. These databases generally include the cytogenetic location, locus, and phenotype of the gene. Examples of such databases included the Online Mendelian Inheritance of Man (OMIM) database maintained by the National Library of Medicine and Johns Hopkins University, which is publically accessible on the internet at http://omim.org; GeneCards (http://genecards.org); the Ensembl genome browser (http://www.ensembl.org); the HGMD® Human Gene Database (http:www.biobase-international.com); UCSC Genome Browser and Gene Sorter (http://genome.ucsc.edu); and GenBank (http://www.ncbi.nlm.nih.gov/genbank).

The term "genotype" as used herein refers to the collective genes of an organism, such as a human, bacterium or virus, and comprises the genetic information of the organism. The "genetic information" comprises heritable biological information or instructions, such as genes, coded in nucleotide sequences of DNA (or RNA), such as in a chromosome. A "phenotype" is an observable expression of an individual's genotype, such as a quantitative trait. Genes may act independently or interact with other genes to influence the phenotype. The term phenotype can also be used to describe a disease state. For example, atherosclerosis is a phenotype of a disease state.

As used herein, the terms "genetic information" and "genetic terms" include any information related to the genotype or phenotype of an organism or microbiome including DNA sequences, RNA sequences, genes and polynucleotide sequences thereof, variant genes and polynucleotide sequences thereof, chromosomes and genes and polynucleotide sequences thereof, genetic mutations, or any such genetic information related to or associated with possible medical findings. The genetic terms can further include molecular targets that may provide a basis for treating a disease, such as a tumor. The molecular targets can be genes expressed, for example, by a tumor or polypeptides encoded by genes in the tumor. Molecular targets generally are genes and the encoded polypeptides that have been identified as having important roles in cell growth or survival such that blocking or interfering with expression of the gene or the activity of the encoded polypeptide can be used to treat a disease, such as regulating tumor cell growth or inducing tumor cell death, such as inducing apoptosis. The molecular targets can also be used to specifically target, for example, tumor cells to stimulate the immune system to recognize and destroy the tumor cells or to deliver a toxic substance directly to the tumor cells.

As used herein, the term "genetic mutation" includes translocation of a gene, nucleic acid substitutions, deletions, or insertions within a gene, single-nucleotide polymorphisms (SNPs) in a gene that result in a change or loss in function of the gene or polypeptide encoded by the gene, overexpression or underexpression of a gene or the polypeptide encoded by the gene, splice variants, truncations, duplications, missense mutations, nonsense mutations, repeat expansions, frameshift mutations, and the like. The term genetic mutation also includes instances where the DNA sequence comprising the gene or the polypeptide encoded by the sequence does not include a mutation within the coding sequence gene, but when, where, or how the gene is being expressed is abnormal and results in or contributes to a disease or condition, such as can be associated with translocation of a gene.

Translocation of a gene or genes is often associated with aneuploidy, infertility, and cancers. In particular, translocation is increasingly being identified as the primary cause of many forms of cancer. Translocation of a gene or genes can result in the disruption or mis-regulation of normal gene function. For example, a translocation may place the coding sequence of one gene in proximity to the regulatory sequence or promoter sequence for a different gene or fuse the coding sequences of two genes together. Hundreds of translocations have been linked to cancer, infertility, or chromosomal disorders and this information is catalogued in publically available databases, such as the Database of Chromosomal Rearrangements in Diseases (dbCRID; which is publically accessible on at http://dbcrid.biolead.org); the HGMD® Human Gene Database (http:www.biobase-international.com); GWAS Central (http://www.gwascentral-.org); GeneCards (http://genecards.org); the Way Station genome variations database (http://www.centralmutation-s.org); and Mutant Reporter (http://www/mutantreporter-.org).

Table 2 shows examples of diseases associated with translocation of genes between chromosomes and describes the translocation at the chromosomal level using cytogenetic notation according to ISCN. The cytogenetic notations of the translocations can be used in the databases herein to describe the gene translocation at the chromosomal level and associate the translocation with a particular medical condition.

TABLE 2

| Translocation | Associated Disease |
|---|---|
| t(12; 21)(p12; q22) | Acute lymphoblastic leukemia (ALL) |
| t(17; 19)(q22; p13) | ALL |
| t(8; 21)(q22; q22) | Acute myeloblastic leukemia (AML) |
| t(1; 12(q21; p13) | AML |
| t(12; 15(p13; q25) | AML; congenital fibrosarcoma; secretory breast carcinoma |
| t(15; 17(q22; q21) | Acute promyelocytic leukemia |
| t(2; 5)(p23; q35) | Anaplastic large cell lymphoma |
| t(8:; 14)(q24; q32) | Burkitt's lymphoma |
| t(9; 22)(q34; q11) | Chronic myelogenous leukemia (CML), ALL |
| t(9; 12)(P24; P13) | CML; ALL |
| t(17; 22) | Dermatofibrosarcoma protuberans (DFSP) |
| t(11; 22)(q24; q11.2-12) | Ewing's Sarcoma |
| t(14; 18)(q32; q21) | Folicular lymphoma |
| t(2; 3)(q13; p25) | Folicular thyroid cancer |
| t(7, 16) (q32-34; p11) or t(11, 16) (p11; p11) | Low grade fibromyxoid sarcoma |
| t(11; 18)(q21;q21) | Mucosa associated lymphoid tissue (MALT) lymphoma |
| t(11; 14)(q13; q32) | Mantle cell lymphoma |
| t(1; 19)(q10; p10) | Oligodendroglioma; oligoastrocytoma |
| t(10; (various))(q11; (various)) | Papillary thyroid cancer |
| t(1; 11)(q42.1; q14.3) | Schizophrenia |
| t(X; 18)(p11.2; q11.2) | Synovial sarcoma |

Additional examples of medical conditions associated with translocation of a gene include prostate cancer, breast cancer, colorectal cancer, ovarian cancer, uterine cancer, bladder cancer, thyroid cancer, pancreatic cancer, mesothelioma, malignant melanoma, hepatocellular carcinoma, retinal blastoma, neuroblastoma, squamous cell carcinoma, non small-cell lung cancer, small cell lung cancer, leukemia, rhabdomyosarcoma, lipoma, lethal midline carcinoma, uveal melanoma, pancreatic neuroendocrine tumors, paediatric glioblastoma, medulloblastoma, glioma, angiomatoid fibrous histocytoma, Hodgkin lymphoma, epitheloid hemangioendothelioma, gastric tumors, aneurysmal bone cysts, multiple myeloma, salivary adenoma, extraskeletal myxoid chondrosarcoma, renal cancer, uterine leiomyoma, clear cell sarcoma, myxofibrosarcoma, fibromyxoid sarcoma, Down's associated ALL, salivary gland mucoepidermoid, cylindroma, sex cord-stromal tumor, embryonal rhabdomyosarcoma, soft tissue sarcoma, desmoplastic small round cell tumor, endometrial stromal sarcoma, idiopathic hypereosinophilic syndrome, granulosa cell tumor of the ovary, alveolar rhabdomyosarcoma, angiomatoid fibrous histiocytoma, Down's Syndrome, megakaryoblastic leukemia, pituitary adenoma, mesenchymal chondrosarcoma, microfollicular thyroid adenoma, Wilm's tumor, intestinal Tcell lymphoma, peripheral T cell lymphoma, parathyroid adenoma, multiple ossifying jaw fibroma; endometrial stromal tumor, clear cell renal carcinoma, and oesophageal squamous cell carcinoma. Cancer genes characterized by translocations, known as oncogenes, are known and can be found, for example, in the OMIM database and the cancer gene census database maintained by the Wellcome Trust Sanger Institute at www.sanger.ac.uk/genetics/CGP/Censes/translocation. The gene census database includes the gene name, locus, Entrez GeneID, cytogenetic location, and translocation partner. These oncogenes and proto-oncogenes (genes that can become an oncogene if mutated or expressed at high levels) are useful markers for diagnose and prognosis of cancer or identifying a genetic predisposition to cancer in a patient.

As used herein, the term "microbiome" and "human microbiome" mean the totality of microorganisms, their genetic information, and the milieu in which they interact. The human microbiome comprises microbial communities that exist throughout the human body, including for example skin, gastrointestinal tract, urogenital tract, oral cavity, naso-pharyngeal tract, blood, abdomen, airways, eye, heart, liver, lymph node, tumor, and wound. The term microbiome can be used to refer to the aggregate population of microorganism inhabiting the human body or to distinct microbial communities within the human body, such as gastrointestinal tract, urogenital tract, oral cavity, naso-pharyngeal tract, blood, abdomen, airways, eye, heart, liver, lymph node, tumor, and wound. Microorganisms associated with the human body include eukaryotes, archaea, bacteria, and viruses. The microorganisms that constitute the microbiome are referred to as the microbiota.

As used herein, the term "metagenome" refers to the collective genes of the microbiome and comprises the genetic information of the microbiome. The metagenome provides information about the functional genetic potential of the aggregate microbial population comprising the microbiome. The term metagenome can be used to refer to the collective genes of the aggregate population of microorganism inhabiting the human body or to the collective genes of distinct microbial communities within the human body, such as gastrointestinal tract, urogenital tract, oral cavity, naso-pharyngeal tract, blood, abdomen, airways, eye, heart, liver, lymph node, tumor, and wound.

Reference sequences for the human microbiome including reference bacterial, viral, and microeukaryotic genomes are known and publically available, for example, at the Human Microbiome Project Consortium assessable at http://www.commonfund.nih.gov/hmp, Human Microbiom Project Data Analysis and Coordination Center accessible at http://hmpdacc.org, and European consortium MetaHIT assessable at http://www.methit.eu. These sequences include the metagenomic assembly and cataloged genes of the microbiome. The 16S ribosomal gene sequences, whole genome shotgun sequences, and reference genome sequences used to construct the metagenomic assembly and gene catalogue are deposited at the National Center for Biotechnology Information and can be publically assessed at www.ncbi.nlm.nih.gov/bioproject/43021.

B. Exemplary Embodiments

Example embodiments described herein allow professional heath care providers a unique opportunity to visualize connections between medical conditions and genetic information from both the human genome and human microbiome, and enable health care providers to more comprehensively investigate all sources and consequences of medical issues, including genes associated with the medical conditions. In some embodiments described herein, systems and methods are provided for utilizing genetic or medical information and presenting related information to caregivers in an easily accessible and visually explanatory format via a graphical user interface. For example, embodiments described below may enable caregivers to view a visual representation of any genes associated with a specific medical finding. In embodiments, the genes visually represented may be associated with the human microbiome and can be used by the caregiver to identify microbes that may be causative or contributing to the medical condition.

In some embodiments, visual representations may include locations of relevant genes within chromosomes, locations of mutations within the relevant genes, or other genes within a relevant gene family comprising a set of genes whose exons are related and generally derived from duplication or variation of an ancestral gene. In some embodiments, the system may enable caregivers to view graphical illustrations depicting the transferal of one or more genes or genetic mutations of interest through generations of a family, thereby enabling caregivers to diagnose possible genetic defects in a patient or carriers of a gene or genetic mutation that may result in a genetic defect or abnormality in offspring of the patient. In yet further embodiments, the system may present visual representations of genes or genetic mutations involved in tumors, including identifying the relevant genes within chromosomes or locations of mutations within relevant genes.

Genetic information can be obtained from a patient by collecting a biological sample from the patient. Examples of suitable samples include but are not limited to skin, hair, tissue, blood, plasma, serum, cells, sweat, saliva, bone, teeth, feces, tissue, biopsy samples, or urine. DNA is extracted from the sample using conventional methods and sequenced to obtain DNA sequences of the patient's genome or microbiome, analyzed to determine the presence or absence of a gene interest in the patient's genome or microbiome, or analyzed to detect and quantify the expression or absence of expression of a gene of interest.

DNA sequencing methods are known and include Sanger type sequencing and Maxam-Gilbert type sequencing. See, for example, Lilan et al., 2002, A Review of DNA Sequencing Techniques, *Quart. Rev. Biophys.,* 35:169-200. Newly developed second and third generation sequencing techniques and instruments allow for low-cost, high-throughput parallel sequencing providing for sequencing of human genomes that is much more rapid than Sanger and Maxam-Gilbert sequencing methods. These next generation sequencing techniques include genomic template preparation and methodologies for processing genomic DNA for downstream sequencing, near-simultaneous or massively parallel generation of millions to billions of short sequence reads, alignment of these sequence reads to a reference sequence, and sequence assembly from the aligned sequence reads. See, for example, Dewey et al, 2012, Clinical Applications of New DNA Sequencing Technologies, *Circulation,* 125:931-944. The high-throughput sequencing platforms include the 454 Genome Sequencer (LifeSciences/Roche) which utilizes pyrosequencing, SOLiD system (Applied Biosystems by Life Technologies) which utilizes sequencing-by-ligation, Illumina genome analyzer (Illumina/Solexa) which utilities easily prepared paired-end sequencing libraries and fluorescently labeled end-blocked nucleotides which are detected by fluorescent imaging and yield image-encoded nucleotide sequences, Complete Genomics Inc. which utilizes sequencing-by-ligation of DNA nano-balls or chained prelicates of 70-bp sequences of shead genomic DNA modified by adaptor inserts, Heliscope (Helicos Corporation) which utilizes single-molecule sequencing by cyclic reversible terminator nucleotide incorporation, Pacific Biosciences' platform for imaging individual DNA polymerase molecules which includes synthesizing a nascent DNA molecule covalently attached to a solid support, Ion Torrent platform (Life Technology) which utilizes a sequencing engine based on detection of hydrogen ions released from nucleotides incorporated into a growing DNA strand, and nanopore sequencing (Oxford) which detects base-specific changes in ionic flux as DNA traverse small pores in solid surfaces placed in an electric field. See, for example, Dewey et al. at Table 1 which shows a comparison of second and third generation sequencing platforms. These sequencing technologies can be used to sequence individual genes, chromosomes, or the whole genome of the patient.

Expression analysis of DNA from the patient can be used to determine the presence or absence of a particular gene or genes in the biological sample from the patient or to detect and quantify the expression or absence of expression of a particular gene or genes in the biological sample. In some embodiments, the expression of a polynucleotide, such as mRNA of a gene or genes of interest is determined. In embodiments, probes or primers to detect gene expression of each gene or the target sequence for each gene are specifically designed. The primers and probes can be designed to specifically identify a gene of interest regardless of whether the gene has sequence variation. Levels of mRNA can be quantitatively measured by Northern blotting in which a sample of RNA is separated on an agarose gel and hybridized to a radio-labeled RNA probe that is complementary to the target sequence. The radio-labeled RNA then can be detected by an autoradiograph.

Another approach for measuring mRNA abundance is polymerase chain reaction. RT-PCR first generates a DNA template from the mRNA by reverse transcription, which is called cDNA. This cDNA template is then used for qPCR where the change in fluorescence of a probe changes as the DNA amplification process progresses. With a standard curve qPCR can produce an absolute measurement such as number of copies of mRNA, typically in units of copies per nanolitre of homogenized tissue or copies per cell. qPCR is very sensitive and detection of a single mRNA molecule is possible. Another approach for measuring mRNA is to individually tag single mRNA molecules with fluorescent barcodes, such as nanostrings, which can be detected one-by-one and counted for direct digital quantification Another approach for expression analysis is gene sequence arrays, such as biochips, DNA chips, DNA arrays, microarrays, and macroarrays. Gene arrays can be used to determine transcript levels for many genes at once, providing an expression profile for the patient. Gene arrays are generally solid supports upon which a collection of gene specific nucleic acid primers or probes have been placed at defined locations, either by spotting or direct synthesis. A nucleic acid sample is obtained from the patient, the sample is labeled, and then the labeled sample is allowed to hybridize with the gene-specific targets on the array. Based on the amount of probe hybridized to each target spot, information is gained about the specific nucleic acid composition of the sample. Examples of commercially available gene arrays include GeneChips® from Affymetrix, Inc. The array or chip can be customized to contain specific combinations of genes from the human genome or microbiome. In embodiments, the array can be configured to contain specific genes from the human genome or microbiome that may be associated with a particular medical condition, such as cancer.

A typical expression analysis for a gene array includes isolating RNA from the patient's biological sample, converting the isolated RNA to labeled complementary DNA (cDNA) via reverse transcription, hybridizing the labeled cDNA to identical nylon membrane or glass array slides, removing unhybridized cDNA, detecting and quantitating the hybridized cDNA, and comparing the quantitative data from various samples.

Another approach for expression analysis employs "tag based" technologies like Serial analysis of gene expression (SAGE), which can provide a relative measure of the cellular concentration of different mRNAs. In other embodiments, the level of expression can be determined using RNA sequencing technology, which generally involves high throughput sequencing of cDNA. The mRNA is isolated and reverse transcribed to form a library of cDNA. The cDNA is fragmented to a specific size and optionally may be detectably labeled. The fragments are sequenced and the full sequence is assembled in accord with different platforms such as provided by Illumina, 454 Sequencing or SOLiD sequencing described above. In addition, mRNA can be sequenced directly (without conversion to cDNA) using protocols available from Helicos.

In embodiments, expression of the polypeptide encoded by the gene or genes of interest is determined. For genes encoding proteins, the expression level can be directly assessed by a number of methodologies similar to the techniques for mRNA quantification described herein. A common method for quantifying protein expression is to perform a Western blot against the protein of interest. The Western blot provides information on the size of the protein in addition to its identity. A biological sample, often a cellular lysate, is separated on a polyacrylamide gel, transferred to a membrane and then probed with an antibody to the protein of interest. Other known methods for identifying and quantifying protein expression include, for example, enzyme-linked immunosorbent assay (ELISA), lateral flow test, latex agglutination, immunochromatography, and magnetic immunoassay.

Genetic information obtained from a patient is stored in the medical information records system described herein and can be accessed or processed as described herein to visualize connections between medical conditions and genetic information from both the human genome and human microbiome, enabling health care providers to more comprehensively investigate all sources and consequences of medical issues.

FIG. 1 illustrates an exemplary embodiment of an electronic healthcare system 100. Caregivers interact with the electronic healthcare system 100 to document patient encounters or access medical information via various user-friendly interfaces. The system 100 includes a medical information records system 102, a network 110, and user computing devices 112. User computing devices 112 include stand-alone computing devices $\mathbf{112}^1$ and $\mathbf{112}^2$ as well as networked computing devices $112^3$ and $112^4$ that are connected to local area network 114.

In general, a health care professional utilizes the system 100 to investigate the causes or resulting medical problems related to a patient's condition. For example, the health care professional can utilize a caregiver interface 118 to search for various medical findings associated with the patient.

Medical findings or findings are medically-related physical or non-physical characteristics about a patient such as a medical complaint; current and past symptoms experienced by a patient; symptoms previously recorded in a patient's medical record; relevant medical history of the patient or patient's family; findings from a physical, psychological, or behavioral examination of the patient; tests performed on a patient and the results of the tests; recorded or possible diagnoses of the patient; therapy or treatment performed or prescribed; medical, psychological, and behavior conditions; procedures, medication taken or prescribed, therapies, genetic information, genetic terms, microbiome information, microbiome terms, and any other medical information related to a patient.

Alternatively, the health care professional can utilize the caregiver interface 118 to search for various genes in the human genome or microbiome which may be causative or contribute to the patient's condition. For example, in some embodiments, a genetic mutation, variant gene, or expression or absence of expression of a gene of interest or combination of genes is causative or contributes to an abnormal medical finding(s). In this way, the health care professional can view a variety of different genes, variant genes, genetic mutations or medical results associated with the patient's condition. This enables the health care professional to investigate alternative medical or external databases to determine the illness severity, illness cause, and appropriate treatment course for the patient. Examples of diseases or disorders are described herein and further include examples of diseases or disorders associated with a variant gene or gene mutation include chromosomal disorders, single-gene disorders, mitochondrial disorders, cancer, and polygenic disorders. Examples of chromosomal disorders include but are not limited to 22q11 deletion syndrome, Angelman syndrome, Beckman-Wiedemann syndrome, branchio-oto-renal syndrome, Cri du chat, Down syndrome, Edward's syndrome, Fragile X syndrome, trisomy X, Turner Syndrome, Klinefelter syndrome, De Lange syndrome, holoprosencephaly, Jacobsen syndrome, Prader-Willi syndrome, Silver-Russell syndrome, Smith-Magenis syndrome, Sotos syndrome, WAGR syndrome, Willians syndrome, orofaciodigital syndrome, gonadal dysgenesis, and Wolf-Hirschhorn syndrome. Chromosomal disorders can also include translocation of genes. Examples of diseases and disorders associated with gene translocation are shown in Table 2. Examples of single-gene disorders include but are not limited to cystic fibrosis, achondroplasia, sickle cell anemia, sickle cell disease, Tay-Sachs disease, myotonic dystrophy, Duchenne muscular dystrophy, Fragile XC syndrome, spinal muscular atrophy, Huntingon's disease, haemophilia haemochromatosis, muscular dystrophy, breast cancer, ovarian cancer, Canavan disease, color blindness, colorectal cancer, cardiomyopathy, gastric cancer, neurofibromatosis, phenylketonuria, and polycystic kidney disease. Other single-gene disorders are known. See for example the listing of over 6,000 identified single-gene disorders at http://www.genecards.org and http://reproductivegenetics-.com. Examples of mitochondrial disorders include but are not limited to mtDNA depletion, MELAS (mitochronidal myopathy, encephalomyopathy, lactic acidosis, stroke-like symptoms), diabetes mellitus, deafness, optic neuropathy, Leigh syndrome, NARP (neuropathy, ataxia, retinitis pigmentosa, ptosis) myoneurogenic gastrointestinal encephalopathy, and myoclonic epilepsy. Examples of cancer include leukemias, lymphoma, breast carcinomas, lung carcinomas, gastric carcinomas, esophageal carcinomas, colorectal carcinomas, liver carcinomas, ovarian carcinomas, thecomas, arrhenoblastomas, cervical carcinomas, endometrial carcinoma, endometrial hyperplasia, endometriosis, fibrosarcomas, choriocarcinoma, head and neck cancer, nasopharyngeal carcinoma, laryngeal carcinomas, hepatoblastoma, Kaposi's sarcoma, melanoma, skin carcinomas, hemangioma, cavernous hemangioma, hemangioblastoma, pancreas carcinomas, retinoblastoma, astrocytoma, glioblastoma, Schwannoma, oligodendroglioma, medulloblastoma, neuroblastomas, rhabdomyosarcoma, osteogenic sarcoma, leiomyosarcomas, urinary tract carcinomas, thyroid carcinomas, Wilm's tumor, renal cell carcinoma, and prostate carcinoma. Examples of polygenic disorders include cancer, autoimmune disease, hypertension, diabetes, obesity, heart disease, atherosclerosis, hypertension, pyloric stenosis, schizophrenia, rheumatoid arthritis, neural tube defects, asthma, psoriasis, epilepsy, cleft palate, Parkinson's disease, and Alzheimer's disease.

Some embodiments of medical information records system 102 include a server 104 and a database 108 that communicate across local area network 106. The database 108 includes various external and internal medical terminologies, and operates to store medical information relating to medical conditions and to send selected portions of the medical information across the network 110 when requested by a computing device 112. The medical information records system 102 can be located at the same location (such as in the same room, building, or facility) as one or more of the computing devices 112. Alternatively, the medical information records system 102 is located remote from the computing devices 112, such as in a different building, city, state, country, or continent.

In some embodiments, the database 108 is coupled to external data sources (shown in FIG. 2) via the network 110. The external data sources may be any external supplier of medical information or data, such as, external electronic medical record systems which allow the system 102 to access patient medical records. The external data sources also may be external libraries, medical terminologies, research sources, or the like which provide the system 102 with updated medical information and genetic terms which can be provided to a caregiver for more efficient review, evaluation, and treatment of patient health.

In embodiments where the system is connected to external data sources, these external data sources may transfer data/information to the medical information records system 102 which utilizes medical terminology that is alternative to the medical information records system 102, and thus translation of the information is necessary for the medical information records system 102 to appropriately use the information. In some embodiments, the database 108 includes a mapping structure that receives medical information (e.g., medical findings) from the other medical records systems and converts then into a terminology utilized by the medical information records system 102. Examples of external terminologies include, but are not limited to, SNOMED CT, ICD-9-CM, ICD-10-CM, the laboratory terminology LOINC, and the drug terminology RxNorm.

The server 104 controls access to records and information stored in medical information records system 102, including records and information stored in database 108. In at least some embodiments, the server 104 is a computing device that includes a database software application, such as the SQL SERVER® database software distributed by MICROSOFT® Corporation. In some other possible embodiments, the server 104 is a Web server or a file server. When a request for a record is received by the server 104, the server retrieves the record from the database 108 and sends it across the network 110 to the computing device 112 that requested it. Some alternative embodiments do not include a server 104, and, instead, computing devices 112 are configured or programmed to retrieve information directly from the database 108.

In at least some embodiments, the server 104 can include a single computer or device for controlling access to database 108 and can be loaded with a file server program for storing, updating, and transferring information in the database 108. In at least some alternative embodiments, the server 104 includes more than one computer. The server 104 also can run a web server for presenting the graphical user interfaces described herein to a caregiver. In these embodiments, the client computing devices 112 executes a web browser for displaying the graphical user interfaces and for enabling a caregiver to interact with the medical information records system 102. In at least some alternative embodiments, the computer code and functionality of the medical information records system 102 is divided between the server 104 and the client computing devices 112. Alternatively, the electronic medical system is stored in and executed entirely by the client computing devices 112.

The database 108 is stored on a data storage device arranged and configured to store a variety of medical information. Examples of storage devices for storing the database 108 include a hard disk drive, a collection of hard disk drives, digital memory (such as random access memory), a redundant array of independent disks (RAID), or other data storage devices. In at least some embodiments records, are distributed across multiple local or remote data storage devices. The database 108 stores data in an organized manner, such as in a hierarchical or relational database structure, one or more tables, or any other suitable structure useful for storing, identifying, and retrieving information. Although the database 108 is illustrated as being separated from the computing devices 112 by the network 110, the database 108 is alternatively a local data storage device of a computing device 112 or is connected to the same local area network 114 as the computing device 112.

The network 110 communicates digital data between one or more computing devices, such as between the medical information records system 102, the computing devices 112, and the external data sources 115. Examples of the network 110 include a local area network and a wide area network, such as the Internet. The network 110 also can be a private network.

In at least some embodiments, the network 110 includes a wireless communication system, a wired communication system, or a combination of wireless and wired communication systems. A wired communication system can transmit data using electrical or optical signals in various possible embodiments. Wireless communication systems typically transmit signals via electromagnetic waves, such as in the form of radio frequency (RF) signals. A wireless communication system typically includes a RF transmitter for transmitting radio frequency signals, and an RF receiver for receiving radio frequency signals. Examples of wireless communication systems include Wi-Fi communication devices (such as utilizing wireless routers or wireless access points), cellular communication devices (such as utilizing one or more cellular base stations), and other wireless communication devices. A wireless communication system also can transmit optical signals.

In at least some embodiments, computing devices 112 are computing devices used by a caregiver and display a caregiver interface 118. The interface can be generated by the caregiver's computing device 112, or they can be generated by a remote computer or server and then transmitted to the caregiver's computing device 112 for display such as a web server that generates a graphical interface and a web browser that remotely displays the graphical interface. Caregivers include physicians, psychiatrists, counselors, therapists, physician assistants, nurses, medical assistants, secretaries, receptionists, or other people that are involved in providing care to a patient. A least some embodiments also may present the user interface to users that are not caregivers, but have a need to access and filter medical findings. In at least some embodiments, a computing device 112 is located at a point of care, such as within a room where a caregiver and a patient interact. A computing device 112 also can be located near the point of care, such as in a hallway or nearby room. However, in other possible embodiments the computing device 112 is not located near the point of care.

The computing devices 112 also can be mobile computing devices that a caregiver can carry from location-to-location or from patient-to-patient. Examples of mobile computing devices include a laptop computer, an ultra-portable computer, a tablet computer (such as Tablet PC® and iPad® devices), a smartphone, or other mobile computing devices. In at least some embodiments, computing devices 112 include a touch sensitive display 156, such as shown in FIG. 2, for receiving input from a user by touching or hovering close to the display 156 with the user's finger, a stylus, or the like.

In at least some embodiments, the electronic medical system 100 includes stand-alone computing devices $\mathbf{112}^1$ and $\mathbf{112}^2$ and networked computing devices $\mathbf{112}^3$ and $\mathbf{112}^4$. Stand-alone computing devices $\mathbf{112}^1$ and $\mathbf{112}^2$ connect directly to network 110 and are not part of an additional local area network 114. The stand-alone computing devices $\mathbf{112}^1$ and $\mathbf{112}^2$ can connect to the network 110 through any suitable technology including a wireless network, such as a cellular telephone network or satellite link, cable modems, ISDN modems. Networked computing devices $\mathbf{112}^3$ and $\mathbf{112}^4$ are connected to a local area network 114 which may be within a facility 116, such as a hospital, clinic, office, or other building. In at least some embodiments, a connection to the local area network is made wirelessly through a wireless access point connected to the local area network. More or fewer computing devices 112 are included in various embodiments and can be located in one or more facilities or locations.

Figure 2:
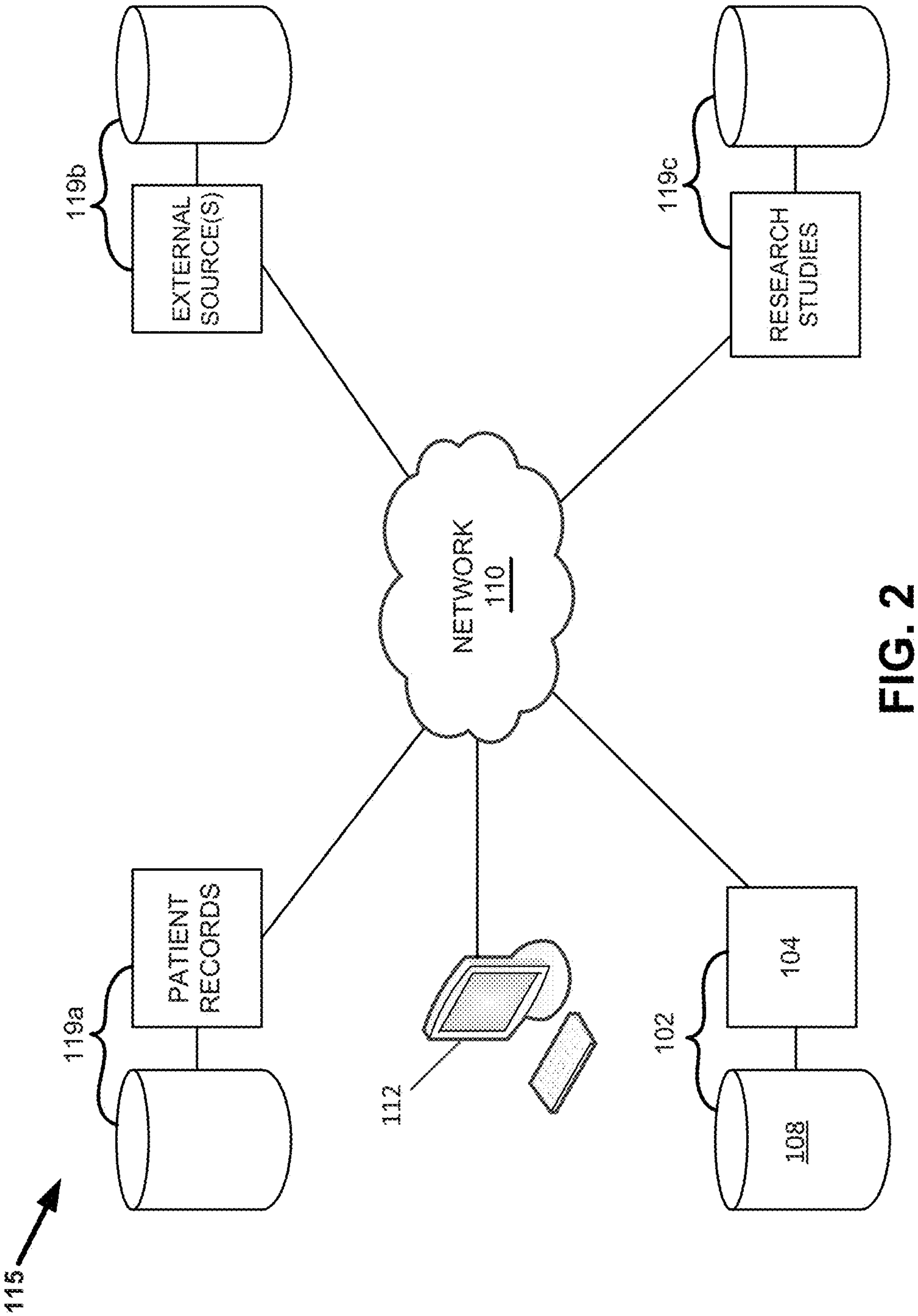
FIG. 2 illustrates an exemplary embodiment of an electronic healthcare system.

FIG. 2 illustrates an alternate embodiment of an electronic healthcare system, in particular, the electronic healthcare system 115. As stated above, caregivers interact with the electronic healthcare system 115 to document patient encounters or access medical information via various user-friendly interfaces. The medical information records system 102, the network 110, and user computing device 112 act in substantially the same way as described above with reference to FIG. 1. The system 115 further includes external data systems 119. In particular, the external data systems 119 include patient records system 119*a*, external data sources 119*b*, and external research studies 119*c*.

The system 102 may utilize external data via the external data systems 119. In some embodiments, the system 102 retrieve particular patient medical records from the records system 119*a*, medical and genetic information from the external data sources 119*b*, or research studies from the external research studies system 119*c*. Data retrieved from the external data systems 119 may be temporarily or permanently stored in the database 108. Alternatively, the system 102 may not store the external data, but instead, continually access information as needed via the network 110.

The patient records system 119*a* provides the system 102 with electronic medical records and other patient recorded medical data. Some examples of electronic medical records systems are described in the co-pending application entitled, "CAREGIVER INTERFACE FOR ELECTRONIC MEDICAL RECORDS," application Ser. No. 12/817,050, the entirety of which is incorporated by reference herein.

The external data sources 119*b* provide updated genetic and or medical information to the system 102. Examples of such data sources 119*b* include, for example, the Online Mendelian Inheritance of Man (OMIM) database maintained by the National Library of Medicine and Johns Hopkins University, which is publically accessible on the internet at http://omim.org; GeneCards (http://genecards.org); the Ensembl genome browser (http://www.ensembl.org); the HGMD® Human Gene Database (http: www.biobase-international.com); UCSC Genome Browser and Gene Sorter (http://genome.ucsc.edu); GenBank (http://www.ncbi.nlm.nih.gov/genbank); PubMed (http://www.ncbi.nlm.nih.gov/pubmed); Protein Data Bank (http://www.wwpdg.org); the Human Microbiome Project Consortium assessable at http://www.commonfund.nih.gov/hmp; the Human Microbiom Project Data Analysis and Coordination Center accessible at http://hmpdacc.org; and the European consortium MetaHIT assessable at http://www.methit.eu. The external research studies system 119*c* provides updated research or case studies regarding genetic and medical information to the system 102. Examples of such systems include PubMed and OMIM.

In some embodiments, external data may enter the system in alternate formats, such as, different medical terminologies or foreign languages. The system 102 may include a translating engine which includes mapping/relationship data which it utilizes to translate data from external medical terminologies into internal medical terminologies. In addition, the translating engine also may translate data from different foreign languages into English or other languages via an internal translator that is provided within the functionality of the translating engine. Examples of how a translating engine may translate the information from external terminologies to internal terminologies are discussed in detail in the following co-pending applications: "INTELLIGENT FILTERING OF HEALTH-RELATED INFORMATION," application Ser. No. 13/772,093, and "ELECTRONIC MEDICAL CODING SYSTEMS", application Ser. No. 13/773,520, the entire disclosures of which are incorporated by reference herein.

Figure 3:
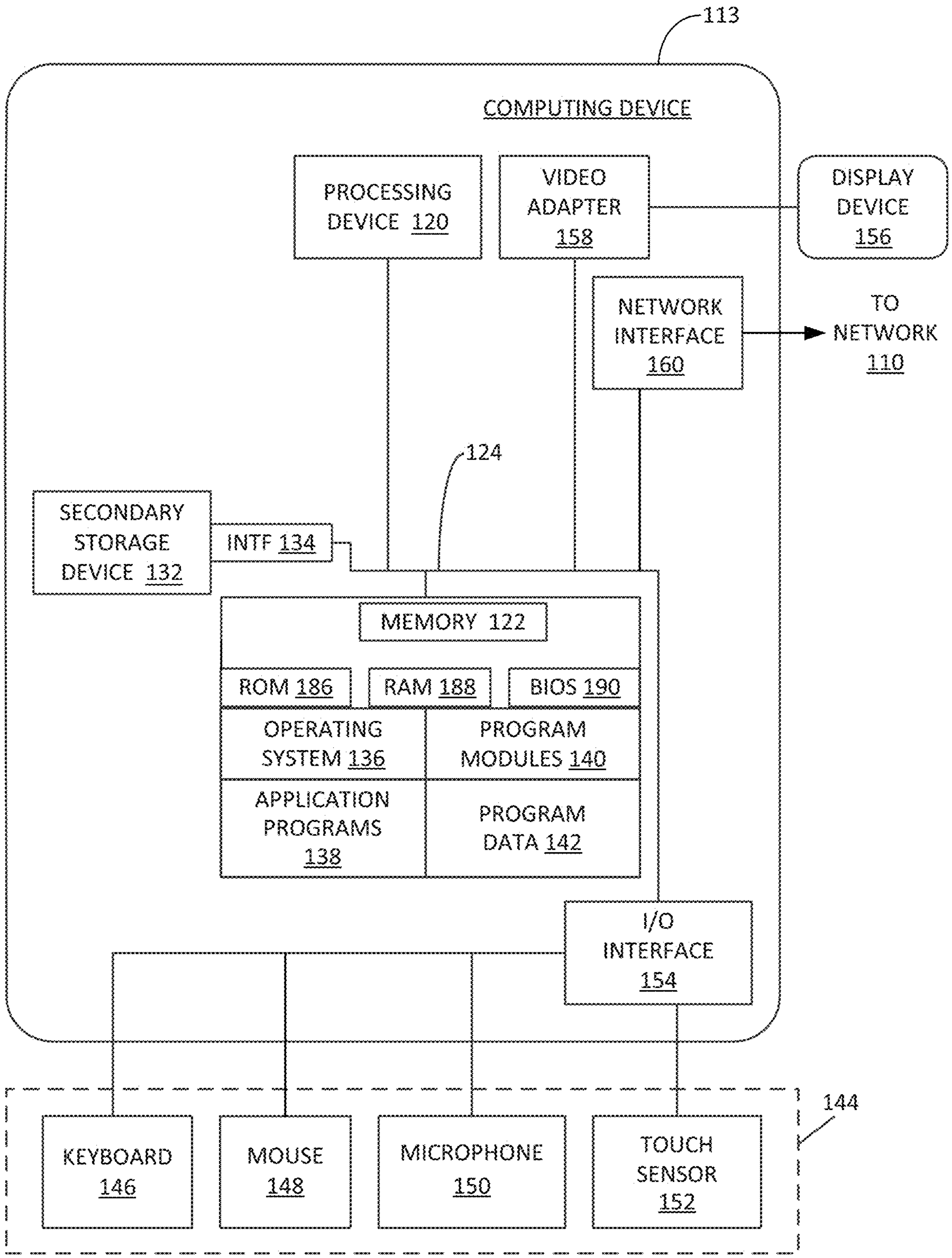
FIG. 3 illustrates an exemplary architecture of a computing device that can be used to implement aspects of the present disclosure.

FIG. 3 illustrates an exemplary architecture of a computing device 113 that can be used to implement aspects of the present disclosure, including the server 104 or the client computing device 112, and will be referred to herein as the computing device 112. The computing device 113 is used to execute the operating system, application programs, and software modules (including the software engines) described herein.

The computing device 113 includes, in at least some embodiments, at least one programmable circuit such as a processing device 120. Examples of processing devices include a central processing unit (CPU) and a microprocessor. A variety of processing devices are available from a variety of manufacturers, for example, Intel, Advanced Micro Devices, Qualcomm, and others. In this example, the computing device 113 also includes a system memory 122, and a system bus 124 that couples various system components including the system memory 122 to the processing device 120. The system bus 124 is one of any number of types of bus structures including a memory bus, or memory controller; a peripheral bus; and a local bus using any of a variety of bus architectures. The computing device 113 also can include a graphical processing unit separate from the processing device 120.

Examples of computing devices suitable for the computing device 113 include a desktop computer, a laptop computer, a tablet computer, a mobile phone device such as a smart phone, or other devices configured or programmed to process digital instructions.

The system memory 122 includes read only memory 126 and random access memory 128. A basic input/output system 130 containing the basic routines that act to transfer information within computing device 113, such as during start up, is typically stored in the read only memory 126.

The computing device 113 also includes a secondary storage device 132 in at least some embodiments, such as a hard disk drive, including magnetic and solid state drives, for storing digital data. The secondary storage device 132 is connected to the system bus 124 by a secondary storage interface 134. The secondary storage devices and their associated computer readable media provide nonvolatile storage of computer readable instructions (including application programs and program modules), data structures, and other data for the computing device 113.

Although the exemplary environment described herein employs a hard disk drive as a secondary storage device, other types of computer readable storage media are used in other embodiments. Examples of these other types of computer readable storage media include magnetic cassettes, flash memory cards, digital video disks, Bernoulli cartridges, compact disc read only memories, digital versatile disk read only memories, random access memories, or read only memories. Some embodiments include non-transitory media.

A number of program modules can be stored in secondary storage device 132 or memory 122, including an operating system 136, one or more application programs 138, other program modules 140, and program data 142.

In at least some embodiments, the data stored in program data 142 can be represented in one or more files having any format usable by a computer. Examples include text files formatted according to a markup language and having data items and tags to instruct computer programs and processes how to use and present the data item. Examples of such formats include markup languages such as html, xml, and xhtml, although other formats for text files can be used. Additionally, the data can be represented using formats other than those conforming to a markup language.

In at least some embodiments, the data stored in program data 142 can be represented in one or more files having any format usable by a computer. Examples include text files formatted according to a markup language and having data items and tags to instruct computer programs and processes how to use and present the data item. Examples of such formats include markup languages such as html, xml, and xhtml, although other formats for text files can be used. Additionally, the data can be represented using formats other than those conforming to a markup language.

In at least some embodiments, computing device 113 includes input devices to enable the caregiver to provide inputs to the computing device 113. Examples of input devices 144 include a keyboard 146, pointer input device 148, microphone 150, and touch sensitive display 156. Various embodiments also may include other input devices 144. The input devices are often connected to the processing device 120 through an input/output interface 154 that is coupled to the system bus 124. These input devices 144 can be connected by any number of input/output interfaces, such as a parallel port, serial port, game port, or a universal serial bus. At least some embodiments also include wireless communication between input devices and interface 154 such as infrared, BLUETOOTH® wireless technology, 802.11a/b/g/n, cellular, or other radio frequency or optical communication systems.

In this example embodiment, a touch sensitive display device 156 is also connected to the system bus 124 via an interface, such as a video adapter 158. The touch sensitive display device 156 includes touch sensors for receiving input from a user when the user touches or hovers a finger or pointer proximal to the display. Such sensors can be capacitive sensors, pressure sensors, or other touch sensors. The sensors not only detect contact with the display, but also the location of the contact and movement of the contact over time. For example, a user can move a finger or stylus across the screen to provide written inputs. The written inputs are evaluated and, in at least some embodiments, converted into text inputs. It is understood that all user selections described herein may be conducted by utilizing a finger to select or move an item on the touch sensitive display device 156. The touch sensitive display can use various different technologies such as resistive, surface acoustic wave, capacitive, infrared grids, projected optical imaging, dispersive signaling, and any other suitable touch technology. User interfaces displayed on the touch sensitive display device 156 can be operated with other types of input devices such as a mouse, touchpad, or keyboard. Other embodiments can use a non-touch display that is operated with an input device such as a mouse, touchpad, keyboard, or other type of input device.

In addition to the display device 156, the computing device 113 can include various other peripheral devices (not shown), such as speakers or a printer.

When used in a local area networking environment or a wide area networking environment (such as the Internet), the computing device 113 is typically connected to the network through a network interface, such as a wireless network interface 160. Other possible embodiments use other communication devices. For example, some embodiments of the computing device 113 include an Ethernet network interface, or a modem for communicating across the network.

The computing device 113 typically includes at least some form of computer-readable media. Computer readable media includes any available media that can be accessed by the computing device 113. By way of example, computer-readable media include computer readable storage media and computer readable communication media.

Computer readable storage media includes volatile and nonvolatile, removable and non-removable media implemented in any device arranged and configured to store information such as computer readable instructions, data structures, program modules or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the computing device 113.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, optical such as infrared, and other wireless media. Combinations of any of the above are also included within the scope of computer readable media.

Figure 4:
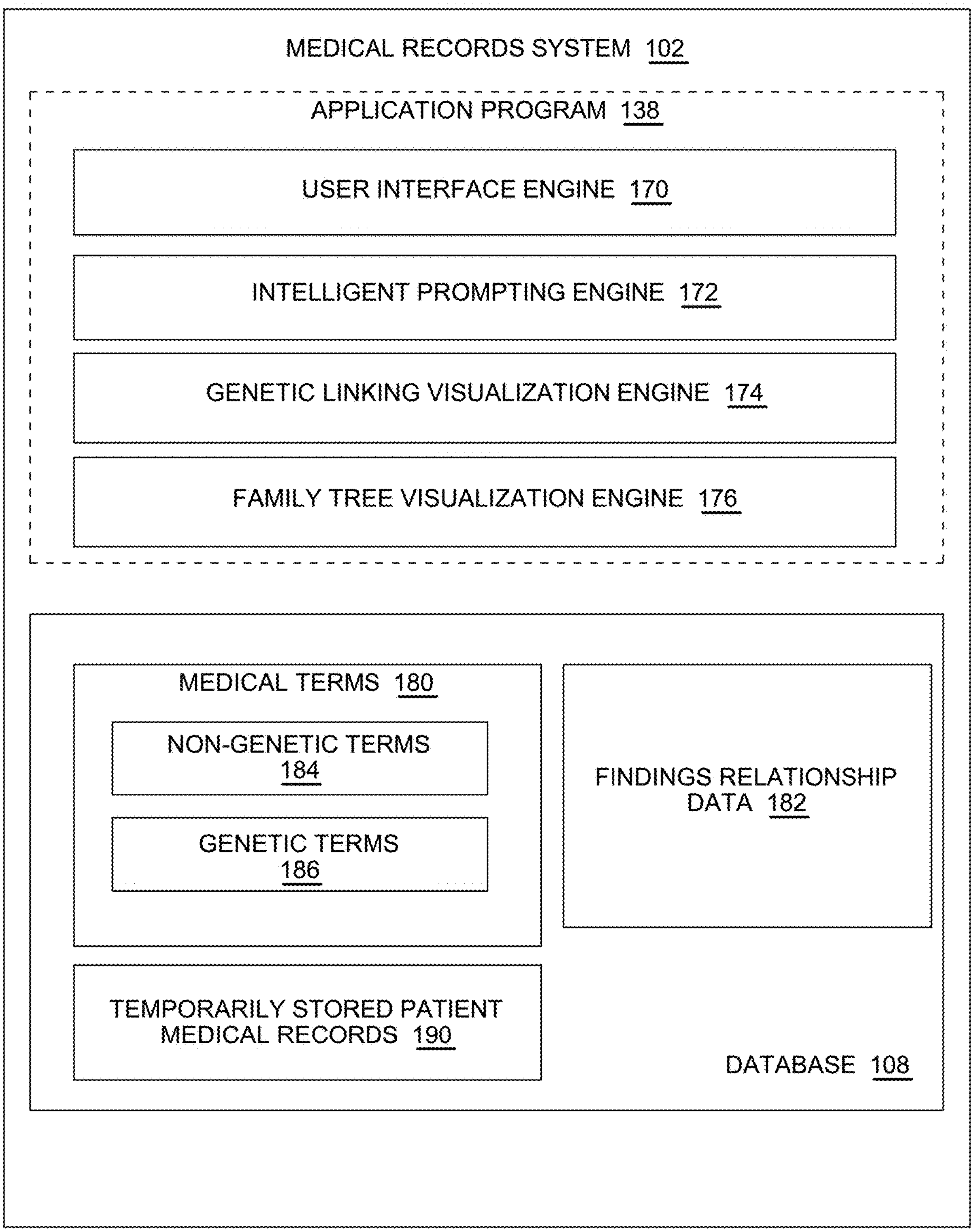
FIG. 4 illustrates an exemplary architecture of an application program of the computing device and a database of the electronic healthcare system.

FIG. 4 illustrates exemplary aspects of the electronic healthcare system 100. As an example embodiment, an application program 138 operates on the computing device 112. In other embodiments, however, the application program 138 operates on one or more other computing devices, such as the server 104. In this example, the medical information records system 102 includes a plurality of engines that, when executed by the processor, perform one or more operations of the application program 138. The engines include a user interface engine 170, an intelligent prompting engine 172, a genetic linking visualization engine 174, and a family tree visualization engine 176. In other embodiments, the plurality of engines could be stored at any other location in the memory 122, such as the program modules 140 (shown in FIG. 3).

The database 108 is stored in one or more data storage devices, such as the memory 122 or the secondary storage device 132 (shown in FIG. 3) of the computing device 112 or another server computing device. The database 108 alternatively can be part of the computing device 112, or selected data can be retrieved from database 108 and stored locally on the computing device 112. The database 108 includes medical terms 180, findings relationship data 182, and temporarily stored patient medical records 190. The medical terms 180 includes non-genetic medical terms 184 and genetic terms 186. The medical terms 180 are medical findings that are utilized by the system 102.

The user interface engine 170 receives inputs from a caregiver. In some embodiments, the inputs are received through the input/output interface 154 (shown in FIG. 3). Examples of such inputs include inputs from a keyboard 146, a pointer input device 148, a microphone 150, or touch sensor 152. In some embodiments, touch inputs are received from a caregiver through the touch sensitive display device 156. Examples of inputs from a caregiver include descriptions or names of medical findings or answers to questions presented to the user through the input/output interface 154 by the intelligent prompting engine 172.

In some embodiments, the intelligent prompting engine 172 utilizes the findings relationship data 182 to present to the caregiver a list of genes related to an inputted medical finding, or alternatively, present to the caregiver a list of medical findings related to one or more inputted genes. Details on how the system 102 intelligently prompts the caregiver based on information stored in the database 108 and how the intelligent prompting engine 172 functions are discussed in detail in the patent entitled, INTELLIGENT PROMPTING, U.S. Pat. No. 5,823,949, issued on Oct. 20, 1998, by Peter S. Goltra, the entire disclosure of which is incorporated by reference herein.

The genetic linking visualization engine 174 provides the functionality to accept an input from a caregiver or an external data source and display, in response, related medical findings. In a at least one embodiment of this scenario, the genetic linking visualization engine 174 may utilize the intelligent prompting engine 172 to present the list of related genes in a graphical display, such as, illustrating the location of each gene within its associated chromosome. In some embodiments, links on the graphical display redirect the caregiver to more information about each of the genes, gene variants, medical findings associated with the gene, causes and risk factors associated with variations of the gene, medical decision support regarding gene variants, possible treatment options, or internal or external case studies and research related to the particular gene/gene variant.

For example, if a caregiver or external data system inputs the medical finding of "Long QT Syndrome" into the system 102, the user interface engine 170 processes the input. The intelligent prompting engine 172 utilizes the findings relationship data 182 to extract genes in the medical terms 180, particularly, the genetic terms 186, which are associated with Long QT Syndrome. In some embodiments, the associated genes are chosen based on a relevance score, which indicates the level of relatedness between the gene and the input. However, in other embodiments, all genes associated with the input are chosen. The genetic linking visualization engine 174 then presents the chosen associated genes in a graphical format for the user. For example, in at least one embodiment, the chosen associated genes are visually presented, such as in an ideogram, so that the user can identify where each gene is located in an associated chromosome. In other embodiments, the genetic linking visualization engine 174 may present information in the genetic terms 186 in alternate viewing formats.

In some embodiments, the genetic terms 186 include genes associated with malignant and benign tumors. In particular, the genetic terms 186 may include genes that are useful for identifying and diagnosing tumors and may include genes that are uniquely expressed by or particular to tumors. For example, the genetic terms 186 may include genes found only within or expressed by growing tumors. In yet further embodiments, the genetic terms 186 include genes and chromosomes within the human body which are known to be affected by tumors or are which may be known to correspond to tumor growths via mutations in a particular gene or the like.

In other embodiments of this scenario, the caregiver may input a gene, such as, "SCN5A" into the system 102. Similarly, the user interface engine 170 processes the input. The intelligent prompting engine 172 then utilizes the findings relationship data 182 to extract medical findings from the medical terms 180, which are related to the SCN5A gene. The findings relationship data 182 includes any pathogenic variants associated with the gene, in this case the SCN5A gene, that are known to be related to medical conditions. The intelligent prompting engine 172 then presents a list of related medical conditions to the user if there is a pathogenic variant associated with the gene that is related to medical conditions.

By viewing either the graphical representation of associated genes or the list of related medical conditions, the caregiver may identify genes or medical conditions which may be afflicting the patient. Thus, the caregiver is in a position to identify a course of further testing or treatment to verify any potential medical conditions associated with the patient. In some embodiments, the graphical representation may be interactive, thus allowing a user to gain more information about specific genes, chromosomes, medical conditions, or medical findings by utilizing an input device to select a link on the interface. For example, in some embodiments, if a user utilizes an input device to click on a gene, a second screen is displayed including further information about the gene.

The system 102 utilizes the database 108 to present the associated genes or medical conditions to the patient. For example, the medical terms 180 includes listings of medical findings and associated medical codes. More specifically, the genetic terms 186 includes a listing of variant genes or genes that are known to have or develop mutations, such as inherited or acquired mutations, translocations, SNPs, deletions, substitutions, insertions, duplications, missense mutations, nonsense mutations, frameshift mutations, and any other medical findings, or information, and associated medical codes. In embodiments, the genetic terms 186 includes a listing of genes that are oncogenes or proto-oncogenes. The non-genetic medical terms 184 includes medical findings, not included in the genetic terms 186, and associated medical codes. The non-genetic medical terms 184 may be referred to herein as "medical items." In some embodiments, the terms in the medical terms 180 are organized for easier filtering by the system 102. For example, the medical terms 180 may include a list of internal medical codes for each item in the medical terms 180. The findings relationship data 182 includes data structures such as tables, lists, matrixes, or the like, which internally connect the various medical findings. In some embodiments, for example, the findings relationship data 182 includes a data structure including a ranking associated with each item in the medical terms 180 indicating the level of relatedness between all other items in the medical terms 180. In some embodiments, this ranking is referred to as a relevance score. An example is illustrated and described in more detail herein, including with reference to FIG. 6.

In other embodiments, the system 102 presents patient medical history to the caregiver in one of several viewing formats. For example, the family tree visualization engine 176 accesses the patient medical records 190 to present a graphical illustration of various portions of the patient's medical history. For example, the family tree visualization engine 176 may access family medical history from the patient, including the patient's genetic data, stored in the patient medical records 190. In some embodiments, the temporarily stored patient records 190 are accessed from a third party site, such as a hospital database or the like. For example, upon authorization, the system 102 may request access to a specific patient record which is then temporarily stored in the database 108. In some embodiments, after a predetermined amount of time, temporarily stored records are deleted from the system.

Examples of information found in the temporarily stored patient records 190 includes blood test results, genetic testing results, histories of conditions, histories of medical procedures, histories of conditions, or any other information related to the genetic makeup of the various family members related to the patient. The engine 176 may access this information and present the data in a viewable format so that the caregiver may more easily determine which medical conditions, symptoms, or genetic defects may be afflicting the patient by studying the patient's family history.

Though the medical terms 180, findings relationship data 182, and patient medical records 190 are described above as being part of the database 108, it is understood that in alternate embodiments of the system 102, one or more of these components (and associated data) are stored externally in one or more of the external data sources 119 (described above with reference to FIG. 2). The system 102 may access this information via the network 110 and temporarily store this information in the database 108. Alternatively, the system 102 may not temporarily store the information, but instead, continually stream this information from the external data sources 119 via the network 110 based on the caregiver's inputs or system needs.

Figure 5:
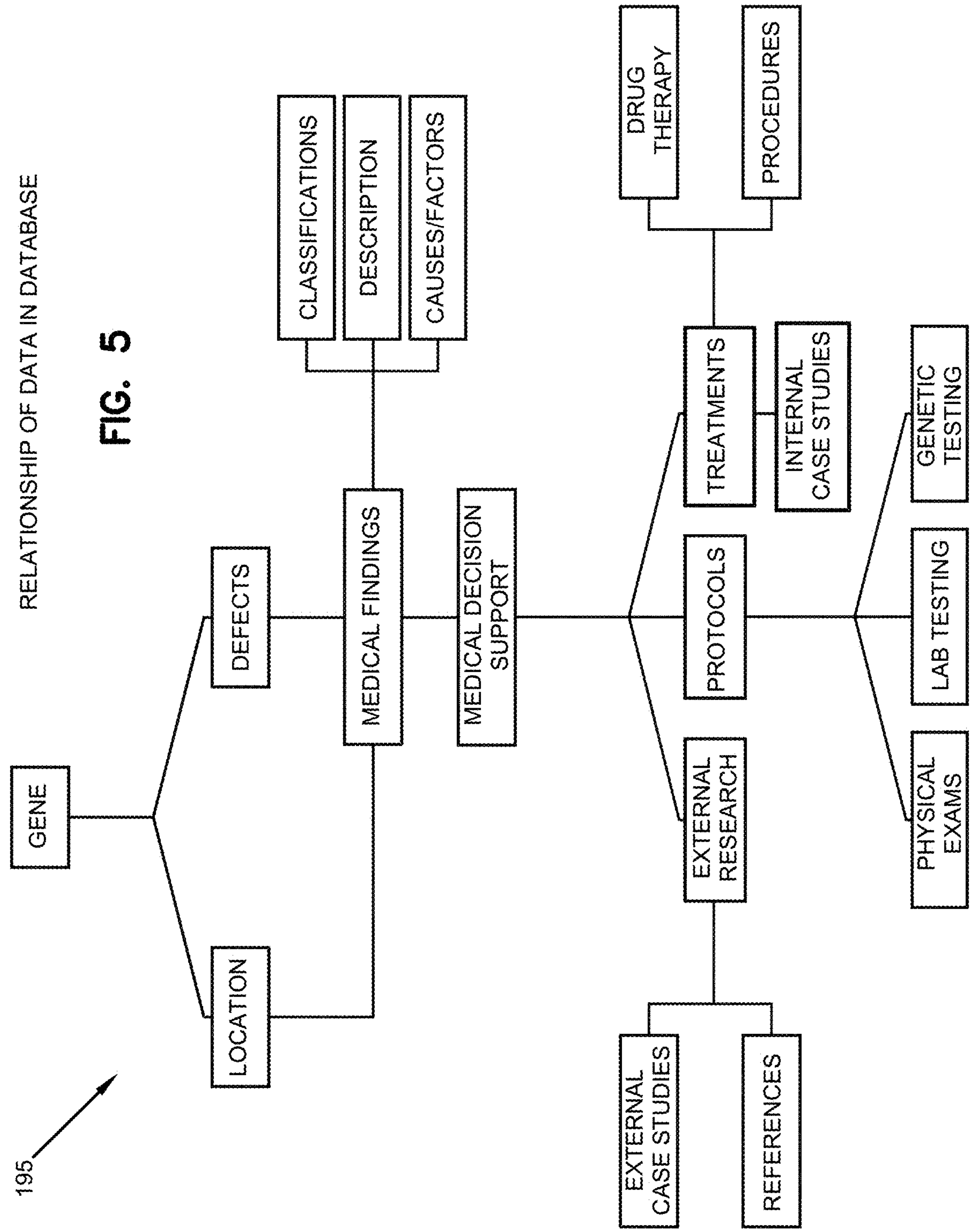
FIG. 5 is an exemplary embodiment of data structures found in the database.

Now referring to FIG. 5, at least one embodiment of a tree 195 which represents an example organization of the data within the database 108 is shown. In general, the tree 195 depicts at least one possible embodiment of the hierarchical structure and interconnectivity of the data (either permanently or temporarily stored) within the database 108. It is understood that though the data is presented as a tree in FIG. 5, this is only one of the possible embodiments for organizing and relating data to one another. The interconnectivity shown in the tree 195 enables linking in the system between different pieces of data. Thus, users may view related data by selecting links presented on a user interface. It is understood that other embodiments of the system 102 may include further relationships not shown in FIG. 5 between items of data.

As illustrated, each gene may include a location within a chromosome and one or more defects associated with the gene. The gene location or defect can be associated with diseases or medical findings. The diseases or medical findings can be associated with classifications, which can be further defined as cardiovascular, pulmonary, muscoskeletal, neurological, or psychological, descriptions which can include disease terms, disease class, and phenotype, causes and risk factors associated with the disease or medical findings, and references or case studies related to the diseases or medical findings. The diseases or medical findings are associated with Medical Decision Support, which can include examination protocols, laboratory testing protocols, genetic testing protocols, case studies, and reference literature. The Medical Decision Support can also be associated with Treatments, which can include drug therapies, including dosage, side effects, and contraindications, surgical procedures, radiation therapy options, including dosage, side effects, and contraindications, and case studies and references. The data in the Medical Decision support can be internal or external to the database 108.

Figure 6:
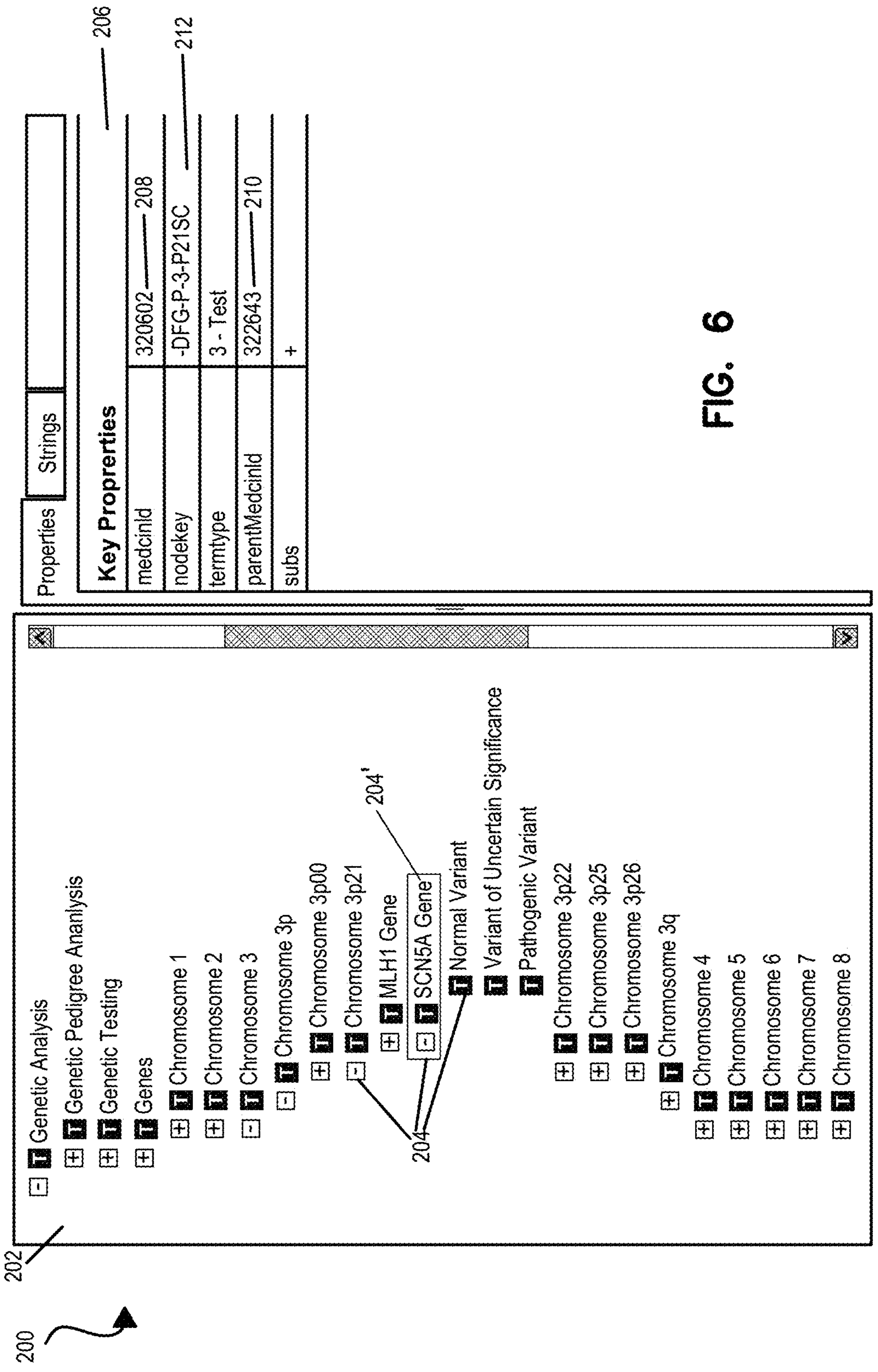
FIG. 6 is an exemplary embodiment of an interactive user interface presented by the electronic healthcare system.

FIG. 6 illustrates an example of an interactive user interface 200 presented by the genetic linking visualization engine 174. In the example, the user interface 200 displays information from the database 108 to the user in a hierarchical format. As shown, the user interface 200 depicts at least portions of the internal organization tree 195 to the user. The user interface 200 includes a genetic hierarchy viewer 202 and a properties viewer 206. The genetic hierarchy viewer 202 includes items 204. The properties viewer 206 displays additional information regarding an item 204' selected from the genetic hierarchy viewer 202, such as an internal medical code 208, a parent medical code 210, and a nodekey 212.

The user interface 200 displays genetic information in the genetic hierarchy viewer 202. More specifically, the genetic hierarchy viewer 202 displays information from the medical terms 180 in a hierarchical format which indicates the order of chromosomes and the location of genes within the chromosomes. As shown, each item 204 includes a heading indicative of information located in the medical terms 180. Some of the items 204 are selectively expandable so that users may view the contents within each item 204. For example, the item "Genes," is expandable to show each chromosome located in the medical terms 180. Each chromosome item is also expandable to show each arm of the chromosome. Further, each arm item is expandable to display any genes positioned within that chromosome arm and the exact location of the gene, for example, by cytogenetic location or chromosomal coordinates. Finally, the genes items are expandable to display any variants of the genes.

In some embodiments, a user selects one of the items 204 to display further information about the item 204. The user may utilize a pointer input device, a mouse, a touch sensor such as a finger or stylus, or any other display selection device to select an item 204. The selected item is then highlighted in the genetic hierarchy viewer 202. For example, in the user interface 200, the term 204' for the SCN5A Gene is highlighted. Once selected, information relating to the item 204' is displayed in the properties viewer 206. In some embodiments, this information includes the internal medical code 208, and the parent medical code 210. In other embodiments, information includes various other internal attributes or identifiers of the selected item. In yet further embodiments, user selection of one of the items 204 results in the user being redirected to medical information about the item. Examples of such screens are described herein and illustrated in FIGS. 10-14.

The internal medical code 208 is the code stored in the medical terms 180 associated with each medical finding, genetic or general. The findings relationship data 182 links this internal medical code 208 with a parent medical code 210, which is also displayed. For example, in the user interface 200, Chromosome position 3p22 would be the parent of the SCN5A Gene. Thus, the parent medical code 210 for the SCN5A Gene would be the internal medical code for Chromosome position 3p22.

The nodekey 212 is an internal tracking number utilized by the system 102 to organize the hierarchical structure of the items in the medical terms 180. For example, the nodekey 212 indicates the tracking number for the item 204'. More specifically, the system 102 associates the nodekey -DFG-P-3-P21SC 212 with SCN5A Gene. In some embodiments, the system 102 will associate the nodekey 212 with the parent nodekey associated with Chromosome 3p22 and the child nodekeys associated with Normal variant, Variant of Uncertain Significance, and Pathogenic Variant. In this way, the system 102 tracks the location of each item in the hierarchical structure.

In some embodiments, a further level is presented in the genetic hierarchy viewer 202 to the user. For example, the viewer 202 may include further child nodekeys beneath a variant, such as, "Pathogenic Variant." The child nodekeys may be, for example, "deletion", "duplication", or "translocation." In this way, the viewer 202 may be able to indicate to the user any conditions associated with the variants. Furthermore, the viewer 202 also may indicate whether a variant is "pathogenic" in nature which indicates that the variant is associated with a particular medical finding, such as an abnormal medical finding(s)abnormal medical finding (s).

Figure 7:
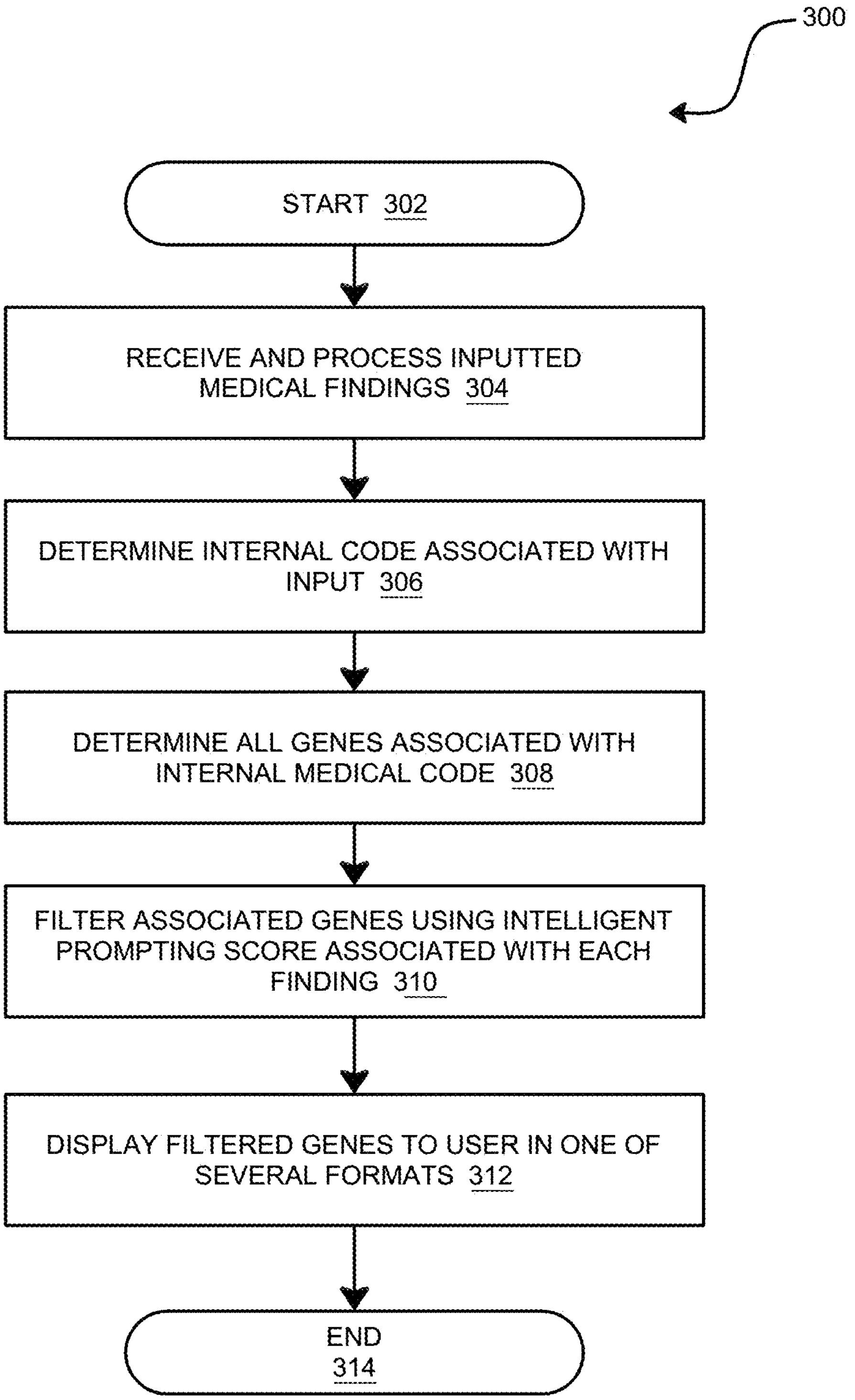
FIG. 7 is a flowchart illustrating an exemplary embodiment of a method of identifying genetic information through a medical information records system.

FIG. 7 is a flowchart illustrating an exemplary method 300 of identifying genetic information through the medical information records system 102. As stated above, a user may be a caregiver who is concurrently examining or has previously examined a patient and is now utilizing the system 102 to determine more information about the patient's medical condition.

The method begins at operation 302. During operation 302, the user of the medical information records system 102 begins interaction with the system and enters an initial input, such as a medical finding. In an alternate embodiment, an input, such as a medical finding, is received at the system 102 by an external data source, such as those described above with reference to FIG. 2. The input may be, for example, "Long QT Syndrome." At this time, the system processes the input at operation 304. In some embodiments, during operation 304, the system determines whether an item matching the input is located in one or more of the medical terms 180. Upon determining that the input is associated with at least one of the medical terms 180, the system determines an internal medical code associated with the input at operation 306. In some embodiments, during operation 306, the system reviews the internal medical terminology 180 to find the internal medical code associated with the input.

At operation 308, the system determines all genes related to the internal medical code associated with the input. In some embodiments, the system accesses the findings relationship data 182 to determine the relationships between the input and any other items in the medical terms 180. For example, inputted medical finding is "Long QT Syndrome," the system accesses an internal table identifying all genes associated with Long QT Syndrome. The table may indicate the level of relatedness between the findings and Long QT Syndrome. In some embodiments, this level of relatedness is called the relevance score, as discussed herein. An example of a table indicating all relevant findings associated with an input can be seen in FIG. 6, discussed in greater detail herein.

At operation 310, the system filters the genes by utilizing a relevance score associated with each finding. For example, the table accessed at operation 308 may include genes that are only minimally related to the input. At operation 310, the system filters any genes below a predetermined relevance score to maximize the relevance of the search results presented to the user. For example, in some embodiments, a relevance score below 2 indicates that the gene does not have a significant relationship with the input. Thus, at operation 310, those genes with a relevance score or 2 or above will pass through the filter and be included in the results. In yet further embodiments, a user is enabled to set the relevance score threshold for filtering. In this way, the user selects the minimum relevance level for the findings. Alternatively, the system may default to a predetermined relevance score threshold.

In some embodiments, the genes associated with the internal medical code may not be filtered. For example, in some embodiments, the system is pre-programmed to skip step 310. In alternative embodiments, the user may choose to skip this step by user selection during the process. This may be useful in situations when the healthcare professional is interested in viewing a broader spectrum of possible results.

At operation 312, the filtered results are displayed to the user in one of several viewing formats. In embodiments when operation 310 is skipped, all results are displayed to the user in one of several viewing formats at operation 312. During this operation, the genetic linking visualization engine 174 may utilize the results and present them to the user at the user interface. In some embodiments, the user can select the viewing format of the results. For example, the user may select between a table of results, list of results, or other graphical representation of the results. For instance, in at least one embodiment, the genetic linking visualization engine 174 presents the user with a graphical illustration, such as an ideogram, of all genes at their location within chromosomes. The genetic linking visualization engine 174 also can present a screen including one or more tables, lists, or information describing the genes associated with the filtered results. At this time, the method terminates at the end operation 314. The user then either begins the process again with a different input or concludes interaction with the system.

Figure 8:
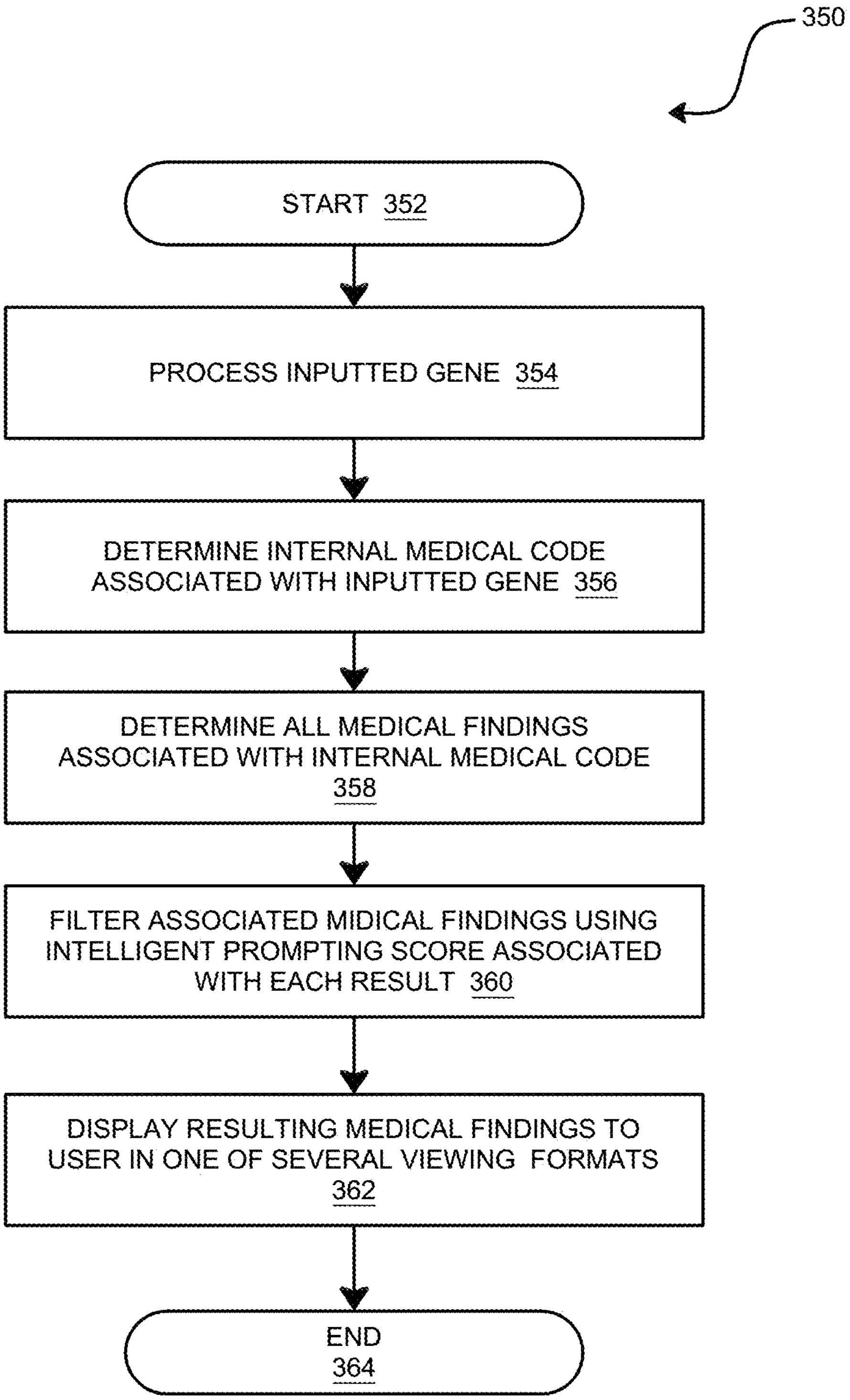
FIG. 8 is a flowchart illustrating an exemplary embodiment of a method of identifying genetic information through a medical information records system.

FIG. 8 is a flowchart illustrating an exemplary method 350 of identifying medical findings through the medical information records system 102. The method includes operations 352, 354, 356, 358, 360, 362, and 364. As stated above, a user may be a caregiver who is examining or has examined a patient and is now utilizing the system 102 to determine more information about the patient's medical condition.

The method 350 is similar to the method 300. However, in the method 350, a gene is inputted into the system at operation 354. Based on the inputted gene, operation 356, similarly to operation 306, determines an internal medical code associated with the inputted gene. Similar methods as those described herein may be utilized. The gene may be inputted in a variety of different ways. For example, the gene may be inputted by a user of the system 102, or transmitted or retrieved from an external data source such as the external data sources described herein and illustrated in FIG. 2.

Upon determining an internal medical code associated with the inputted gene, the system 102 determines medical findings associated with the internal medical code at operation 358 similarly to operation 308. For example, if the gene is "SCN5A," operation 358 may determine a list of medical findings often present in patients having a malfunction associated with the SCN5A gene.

In operation 360, a similar filtering process as that described with reference to operation 310 occurs. However, as disclosed herein with respect to at least some embodiments, a filtering process may not occur and instead, all medical findings associated with the gene are presented to the user in operation 362. In operation 362, as disclosed herein, several different viewing options may be selected from or chosen by the system to present the medical findings similar to operation 312. For example, in at least one embodiment, the results may be presented to the user in a table format for easy viewing by the healthcare professional.

FIG. 9 is a schematic diagram 400 illustrating a filtering process conducted by the medical information records system 102. The filtering process is an example of what occurs during operations 310 and 360, and as discussed herein. The diagram 400 includes a full results table 402 and a filtered table 404. The full results table 402 includes a descriptions column 406, an internal medical code column 408, a relevance score column 410, and a nodekey column 412. Each column includes items a-e, respectively. The filtered table 404 includes a filtered descriptions column 414, a filtered internal medical code column 416, a filtered relevance score column 418, and a filtered nodekey column 420. Each column in the filtered table 404 includes items a-c, respectively.

The full results table 402 is an example of all medical findings associated with an input, "Long QT Syndrome." The table 402 is an example of a table stored in the findings relationship data 182. The table 402 is an example of all genes known by the system 102 to be associated with the input, "Long QT Syndrome." For example, in the table 402, five genes, SCN5A, KCNQ1, KCNH2, KCNJ2, and KCNE1, located at 406_a-e_, respectively, are shown. In alternate embodiments, the findings relationship data 182 may store various tables of different lengths, having differing results for each medical finding stored in the medical terms 180. In the example, the system 102 has determined that the genes 306*a-e* are the only relevant medical findings associated with Long QT Syndrome.

The description column 406 describes the medical finding. In some examples, the column 406 includes genes. In alternate embodiments, the description column 406 includes medical findings. In yet further embodiments, the description column 406 includes a combination of information found in the medical terms 180. The table 402 also includes internal medical codes 408*a-e* associated with each finding. As discussed above, the system 102 utilizes the internal medical codes 408*a-e* to internally identify each finding.

Further, the table 402 includes relevance scores 410*a-e*, indicated by acronym RS. The relevance scores indicate the level of relatedness between the finding and the input. The scores are pre-calculated and stored in the findings relationship data 182. In some embodiments, such as the present embodiment, the scores range from 0-3, where a lower number indicates a lower level of relevance with the associated input. In other embodiments, however, alternate scoring methods are utilized to achieve the same result.

The table 404 is an example of a filtered table of relevant results for Long QT Syndrome. As shown, only the medical findings with relevance scores of 2 or greater were selected from the table 402. As discussed above, the system 102 may utilize a predetermined relevance score threshold for filtering purposes. In alternate embodiments, the user indicates which relevance scores should be filtered. In the present embodiment, the genes KCNQ1 and KCNJ2 were not included as part of the results in the filtered table 404 because their respective relevance scores fall below a default relevance score threshold of 2.

Figure 10:
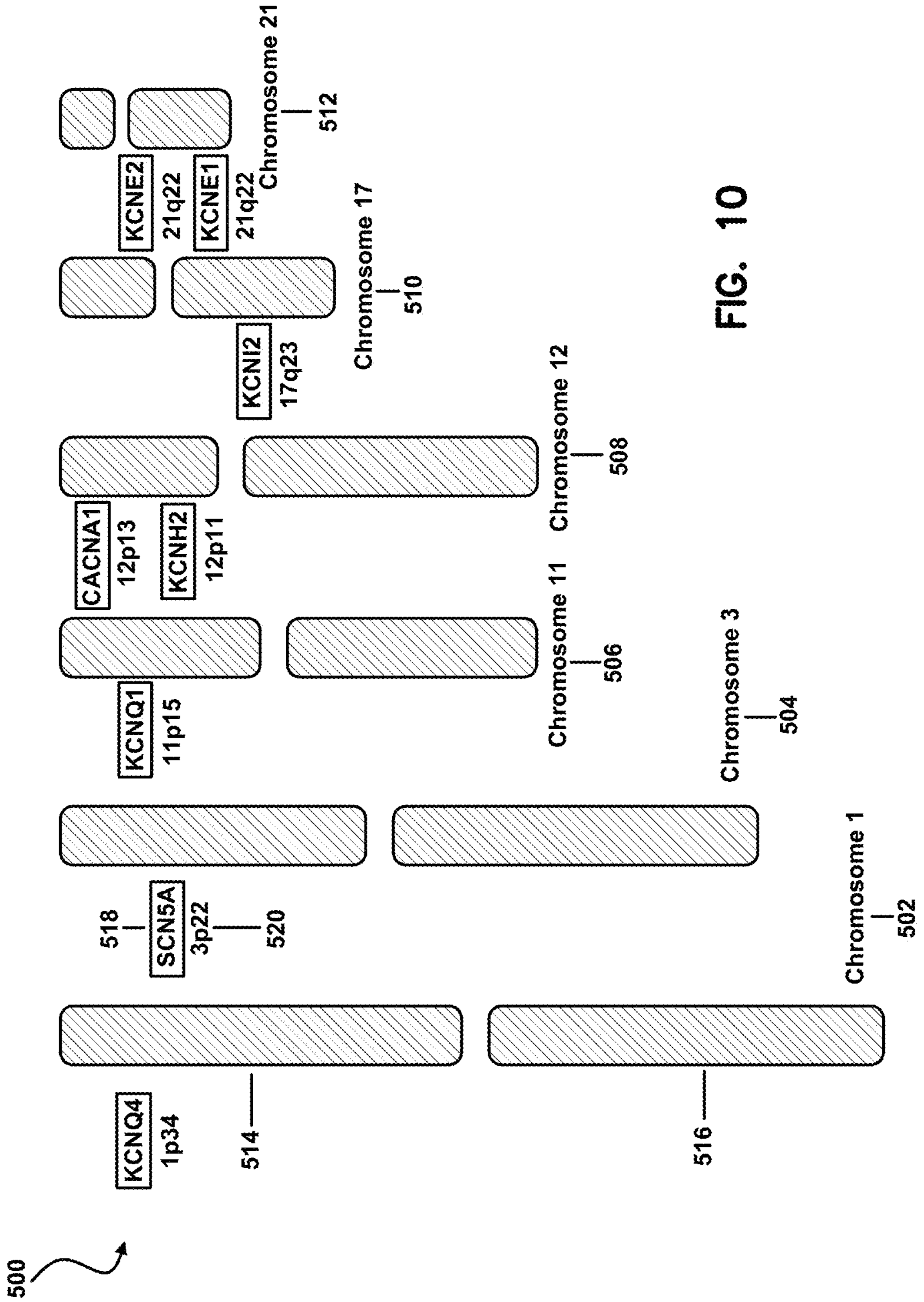
FIG. 10 is another exemplary embodiment of an interactive user interface presented by the electronic healthcare system.

Now referring to FIG. 10, an example graphical user interface 500 is shown. The display 500 includes chromosomes 502, 504, 506, 508, 510, and 512. Each chromosome includes a p arm and a q arm, such as p arm 514 and q arm 516 for chromosome 502. Some p and q arms include genes, such as gene 518. Any displayed gene also includes a location, such as location 520. In general, the user interface 500 is an example of intelligent prompting results presented to a user. For example, a user may input a medical finding that a patient is experiencing, and the system 102 may output, in response, the user interface 500 which displays possible genes associated with the medical finding and their proper locations within corresponding chromosomes. A user may utilize the user interface 500 to determine potential genetic defects affecting the patient based on his health complaints. In this way, the system 102 enables a caregiver to review possible genetic conditions and gain different perspectives to properly assist in the ultimate evaluation and treatment of the patient.

The display 500 is an example of a viewing format displayed by the genetic linking visualization engine 174. In the example, the relevant and filtered genes, SCN5A, KCNQ1, KCNH2, and KCNE1 are presented in a graphical format for the user. In the present embodiment, the genes are illustrated at their locations within chromosomes. For example, the gene SCN5A is located at the p arm of Chromosome 3 at the location 3p22. The display 500 indicates the approximate location of 3p22 by positioning the gene identifier on the chromosomal arm at a specific point. Similarly, the other relevant genes are positioned at approximate locations associated with their known positions.

The display 500 provides the caregiver an opportunity to view the filtered medical findings in a viewing format that assists the caregiver in identifying and studying genes/genetic variants that may be afflicting the patient. Furthermore, by indicating the known locations of the relevant genes, the display 500 enables the caregiver to determine whether the patient's genes are located at their proper locations. In this way, the caregiver may be able to determine whether the patient is suffering from an affliction directly or indirectly related to a translocation of a gene. The display 500 also identifies the genes in a format that enables the caregiver to quickly and efficiently determine potential problematic genes and thereby determine which further testing or treatment may need to be administered to the patient.

In some embodiments, the display 500 illustrates the mutations of the displayed genes. For example, the display 500 may show the polynucleotide sequence of the gene and indicate mutations, such as substitutions, deletions, insertions, duplications, missense mutations, nonsense mutations, and frameshift mutations, in the polynucleotide sequence. In some embodiments, the display 500 shows, for example, a mutation of a gene (e.g., deletion), where the mutation occurs, or a code that identifies the particular mutation. The identification code may be a four or five letter code (e.g., "L123F") that identifies the particular mutation. In addition, the display 500 may further include a description of the mutation for the user.

In some embodiments, the display 500 includes alternate displays. For example, the display 500 may include a visual representation of the genetic makeup of a benign or malignant tumor. The display 500 may include genes and chromosomes found only within tumors. In other embodiments, the display 500 may include genes and chromosomes found within the human body which are known to relate to tumorous growths. In such embodiments, the display 500 may be generic to known tumor growths.

In other embodiments, the genetic linking visualization engine 174, may access the temporarily stored patient medical records 190 to present a visualization of a genetic sequencing of a particular patient's tumor. For example, a caregiver may input a patient's name or identification code, and the system may utilize the input to access the particular patient's information and extract any tumor sequencing information found in the record. The system may further access the genetic terms 186 associated with tumors to determine genetic terms related to the particular patient's tumor sequencing information. Thus, the display 500 may include genes and chromosomes specific to a particular patient's benign or malignant tumor. A caregiver may utilize the display 500 to identify particular genes or chromosomes within the particular patient's tumor to determine appropriate causes or treatments.

As stated above, the genetic terms 186 can include molecular targets that may provide a basis for treating, for example, a tumor. For example, the system may access the genetic terms 186 to determine molecular targets related to the particular patient's tumor sequencing information and display a listing of candidate molecular targets for treating the tumor. The display 500 may additionally provide information about drugs, such as small molecule drugs and antibodies, having specificity for the identified molecular targets including dosage, side effects, contraindications, and case studies.

The display 500 may incorporate one or more links as well. In particular, a user may utilize an input device to select one or more images or words on the display 500 for further information about the selected item. For example, users may select genes and chromosomes to view further information about these items, including, for example, other genes that respond to stimulation similarly to surrounding genes, other medical findings associated with the genes, causes and risk factors related to or concerning the gene and any associated genetic defects, treatment options, case studies, or internal or external research on the selected item.

Figure 11:
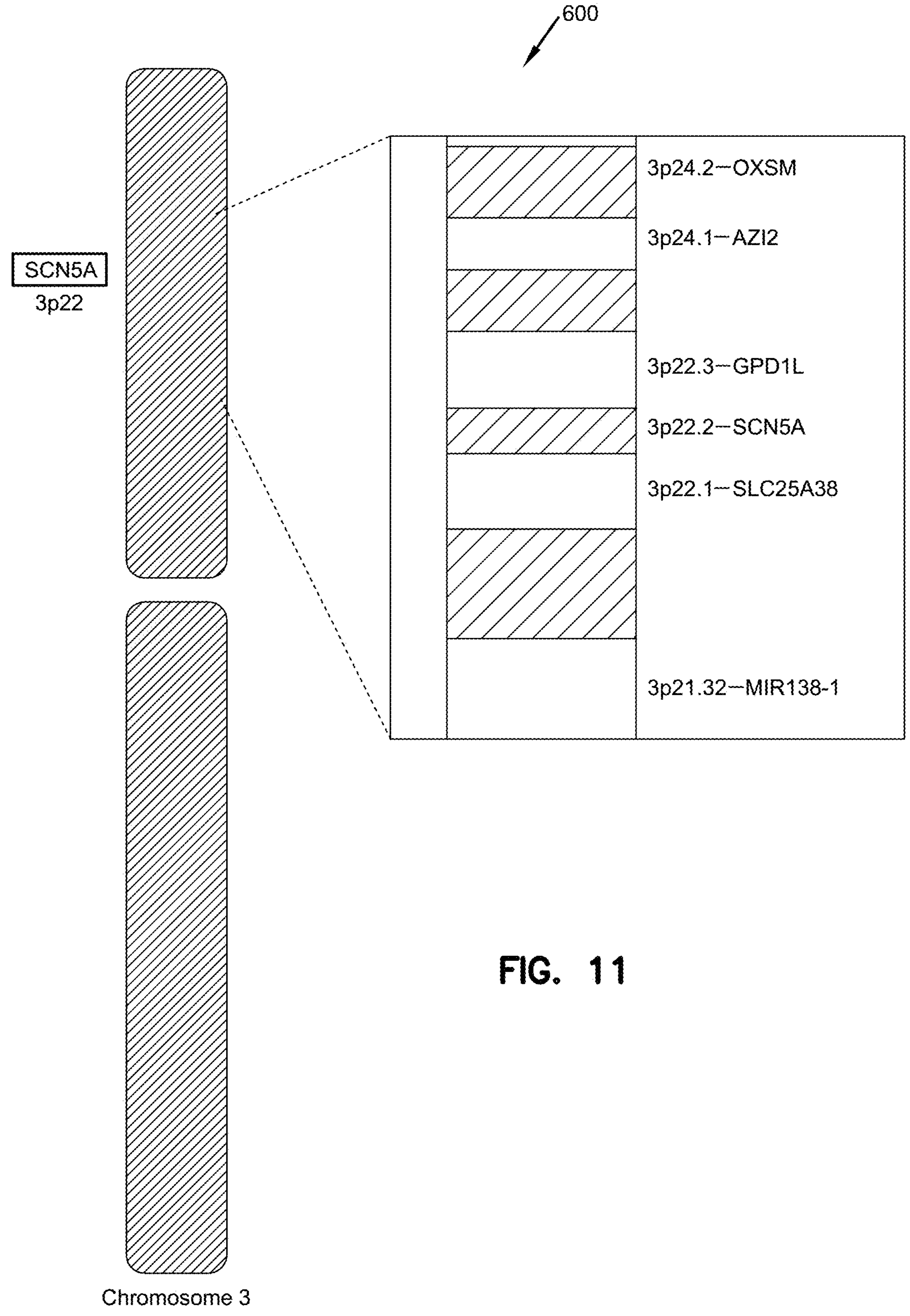
FIG. 11 is yet another exemplary embodiment of an interactive user interface presented by the electronic healthcare system.

Now referring to FIG. 11, an example user display 600 is shown. The display 600 is an example of a display that is presented to the user upon clicking a gene on the display 500. In the present example, the display 600 depicts further information about the gene of interest, SCN5A.

In particular, FIG. 11 illustrates other genes located on the p arm of chromosome 3, so that the user can view the location of the gene of interest in relationship to other genes of chromosome 3 and other genes that may be affected by variations in the SCN5A gene or upon which the gene of interest may exert control.

Figure 12:
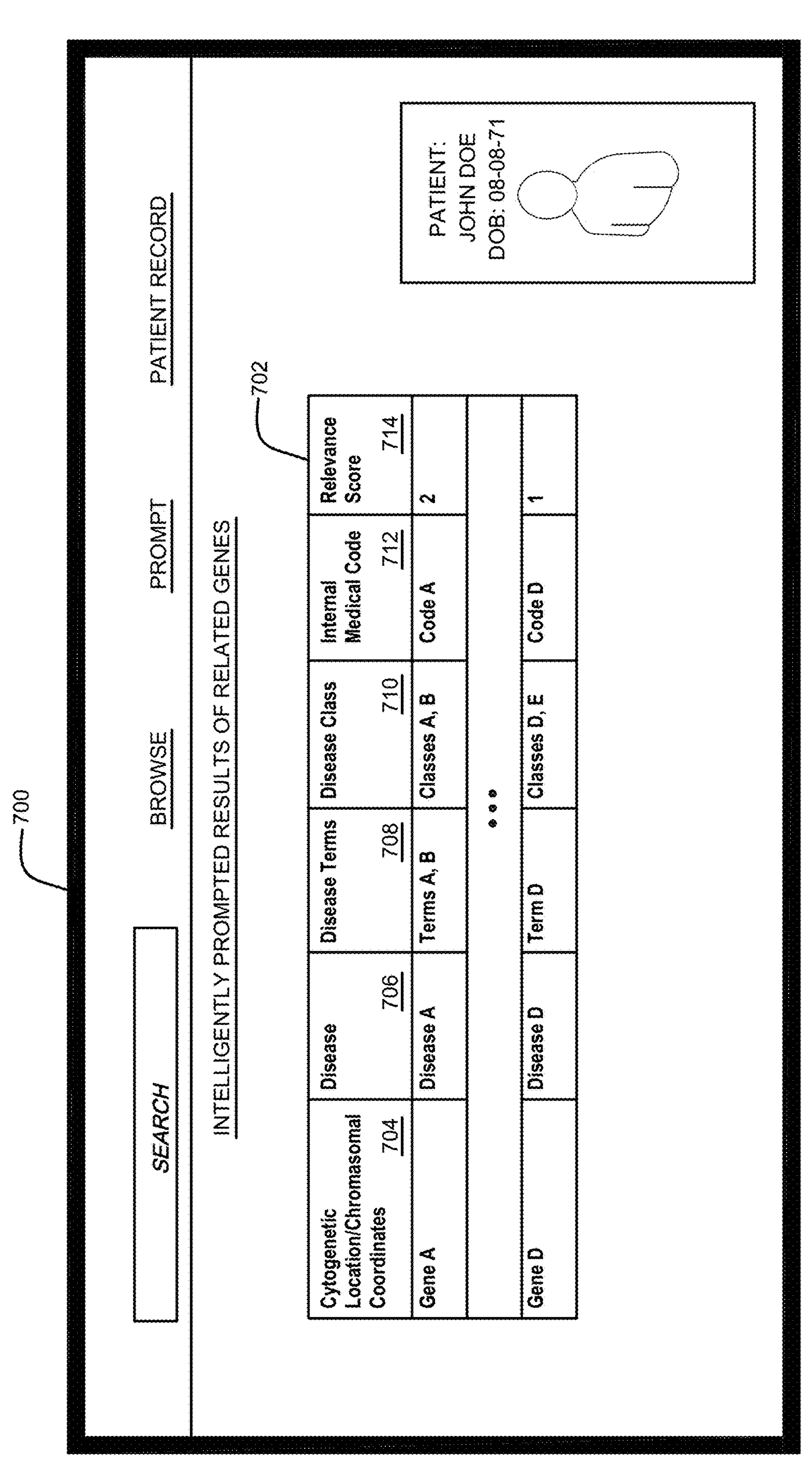
FIG. 12 is yet another exemplary embodiment of an interactive user interface presented by the electronic healthcare system.

FIG. 12 depicts user display 700. The user display 700 is an alternate example of the display 500. More specifically, the display 700 includes a table 702 which includes relevant genes associated with an inputted medical finding. The table 702 includes a gene column 704, a disease column 706, a disease term column 708, a disease class column 710, an internal medical code column 712, and a relevance score column 714. It is understood that alternate embodiments of the table 702 may include less columns than presented, or more columns including other relevant information for a user.

In the example, the relevant genes, Gene A and Gene B each further include associated diseases, disease terms, disease classes, internal medical code, and relevance scores. Examples of disease classes include aging, cancer, cardiovascular, chemical dependency, developmental, hematological, immune, infection, metabolic, mitochondrial, neurologic, normal variation, other, pharmacogenomic, psychiatric, renal, reproduction, vision, and unknown. The disease terms include medical terminology descriptive of the disease class or phenotype of disease. The internal medical code is used to internally identify the gene in the system 102 and the relevance score, as described above, indicates the relevance level of the gene to the user-inputted medical finding.

A user may utilize the display 700 to identify potential gene defects in a patient. For further information, in some embodiments, the user may click on links associated with each text item in the table 702. For example, the use may select "Disease A" to be redirected to a page including detailed information on Disease A. In yet further embodiments, a pop-up with information may appear upon selecting text in the table 702.

Now referring to FIG. 13, a user display 800 is shown. The display 800 is an example of a display that is presented to the user upon selection of a gene in either one of the displays 500, 600, or 700. As shown, the display 800 includes a variety of information on the selected gene, in this example, Gene A. For example, the display 800 includes a list 802 listing medical findings, causes, risk factors, references, genetic information, medical decision support, treatment options, and case studies associated with Gene A. In the example, the list 802 is expanded; however, it is understood that in alternate embodiments, items on the list, such as item 804 is selectively expandable to view the sub-items beneath the selected item. Additionally or alternatively, each item is selectable to view more information on that particular item. In the case of case studies and references, in some embodiments, links may redirect a user to an external source, such as an external database or website.

In the list 802, a "Genetics" header is presented. This header includes information particularly relevant to Gene A. For example, biophysical or functional characteristics of the gene or defects in the gene, the polynucleotide sequence of the gene, genetic variants of the gene including polynucleotide sequences of any genetic variants, an ideogram (such as in FIG. 11 or 12 showing the location of the gene and surrounding gene in the chromosome), and references related to the gene, such as articles from scientific or medical journals.

Figure 14:
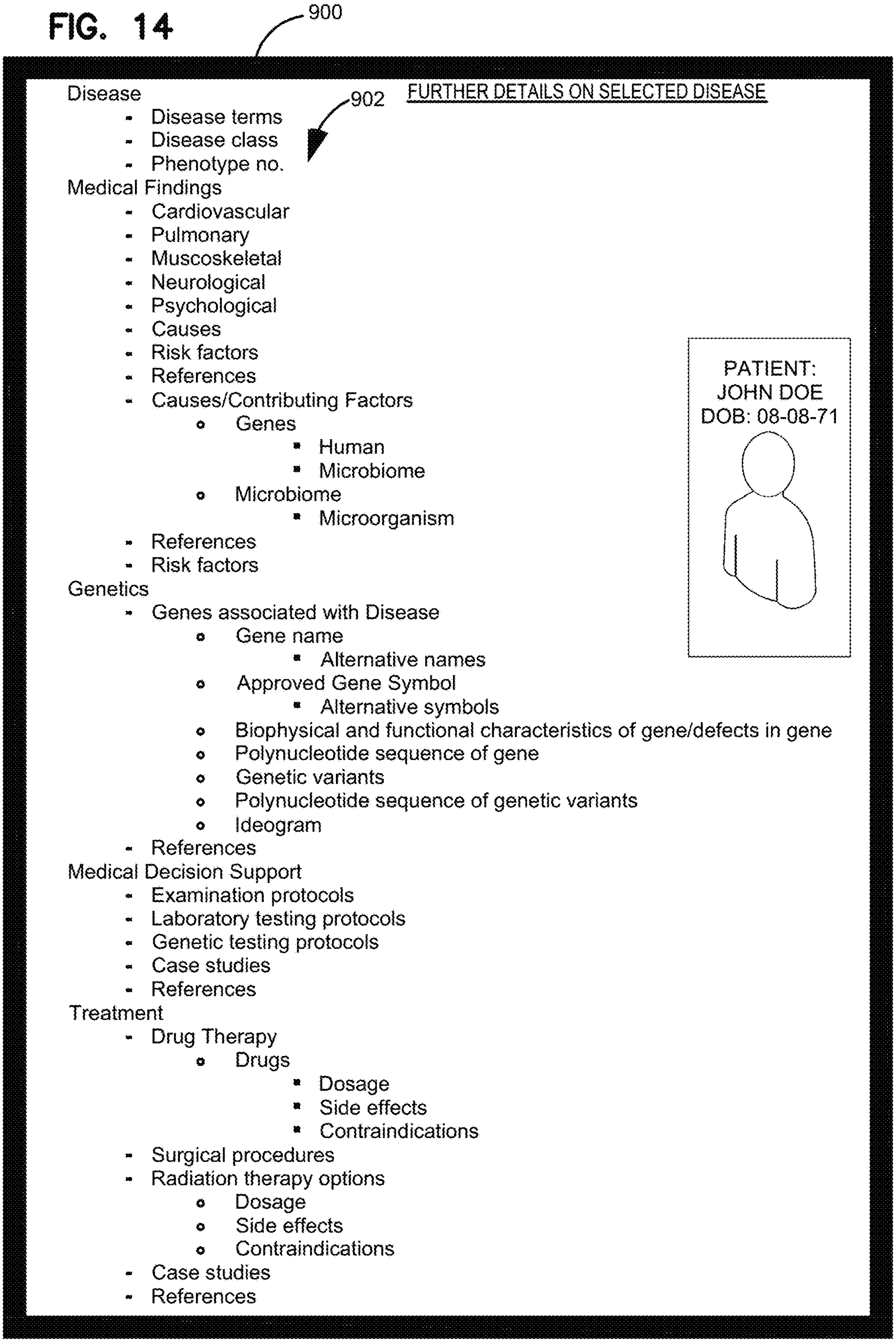
FIG. 14 is yet another exemplary embodiment of an interactive user interface presented by the electronic healthcare system.

FIG. 14 depicts a user display 900. The user display 900 is an example of a display that is presented to the user upon selecting a disease, such as Disease A or B, in the user displays 700 and 800 for further information. The user display 900 includes a list 902. Similarly as described above, the list 902 may be selectively expandable like the list 802. In general, the user display 900 includes the similar information as that discussed above with reference to the user display 800, however, in the particular example, the information is related to the selected disease instead of the selected gene.

Figure 15:
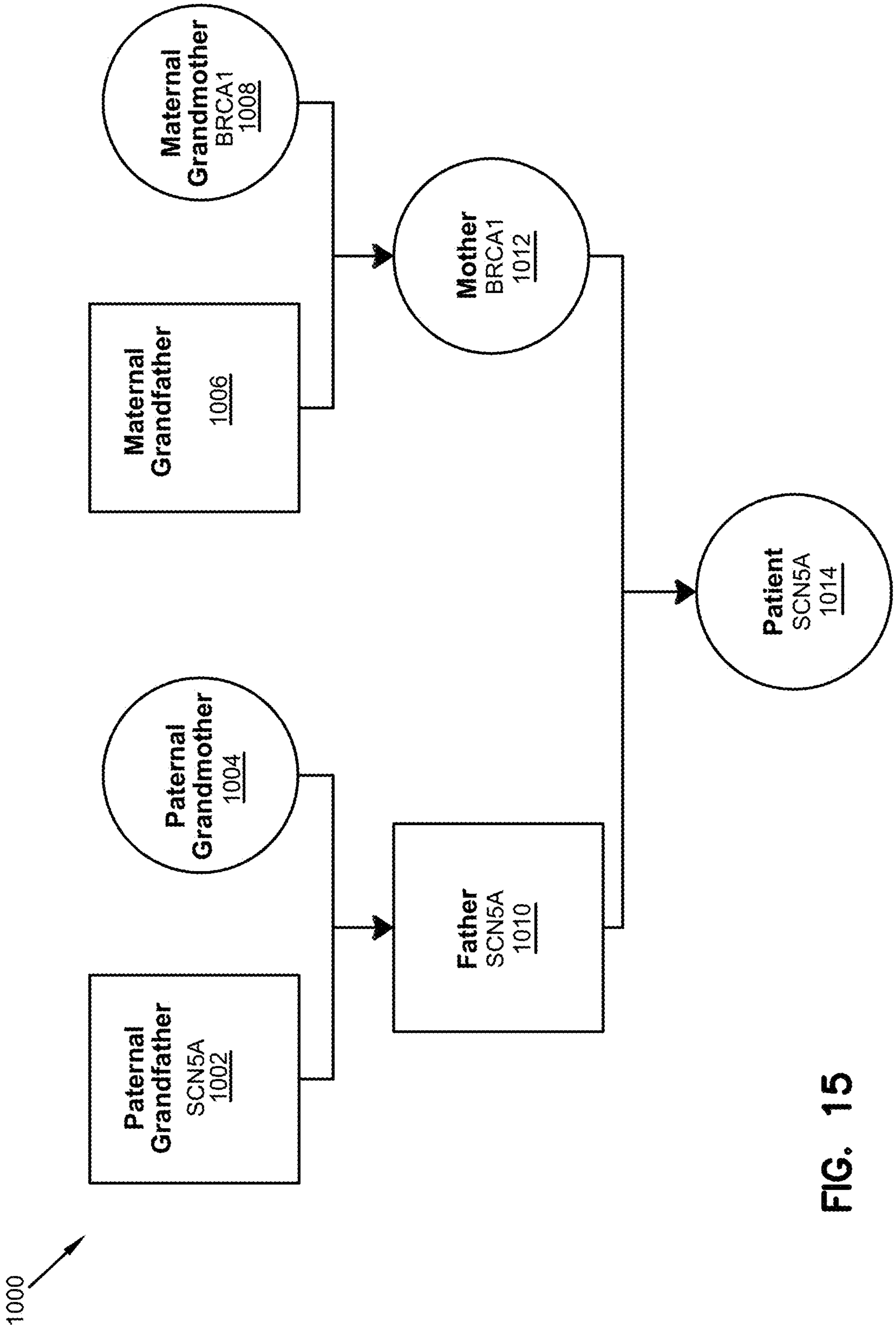
FIG. 15 is yet another exemplary embodiment of an interactive user interface presented by the electronic healthcare system.

Now referring to FIG. 15, an example user display 1000 is shown. The display 1000 includes an example of family relationship data presented to a caregiver in a user-friendly format. The display 1000 is an example of a viewing format presented by the family tree visualization engine 176 after accessing data stored in the patient medical records 190. The display 1000 includes boxes indicative of paternal grandfather history 1002, paternal grandmother history 1004, maternal grandfather history 1006, maternal grandmother history 608, father history 1010, mother history 1012, and patient information 1014.

In the example, the display 1000 shows the history of defects of the genes SCN5A and BRCA1 in the patient's history. The display 1000 may display medical findings. In the example, the caregiver utilizes the display 1000 to determine the possibility of genetic defects in the patient or the origin of genetic defects in the patient by seeing or visualizing medical findings or other information that is similar from generation-to-generation or that carries from ancestor to descendant. The display 1000 may include a probability that the patient may suffer from a genetic disorder associated with a specific gene or genes or be a carrier of pathogenic variant gene that may be passed to offspring.

In some embodiments, upon discovering that the patient has a genetic defect, the information may be used to trace the origin of the genetic defect. For example, a user of the system may utilize the display 1000 to determine whether the source of the genetic defect is maternal or paternal. In some embodiments, the user may further determine, based on this information, whether other relatives of the patient or maternal/paternal source also may suffer from the genetic defect.

In some embodiments, the caregiver may utilize the display 1000 in conjunction with an alternate display such as, for example, the display 500 (shown in FIG. 10). For instance, the caregiver may review the display 500 and determine that mutations in three genes, SCN5A, KCNH2, and KCNE1, may be the cause of the patient's Long QT Syndrome. After reviewing the display 1000, the caregiver may determine, for example, that although two genetic mutations exist in the patient, one relating to SCN5A and one relating to BRCA1, in view of the display 500, it is likely that the cause of the patient's Long QT Syndrome is associated with the SCN5A gene. In this way, the displays 500 and 1000 enable the caregiver to more accurately and efficiently sift through potential causes of the abnormal medical finding(s)abnormal medical finding(s).

In some embodiments, the caregiver can select one of the boxes 1002, 1004, 1006, 1008, 1010, 1012, or 1014, or associated text, to view further information about the medical histories. The caregiver also may select one or more of the genes SCN5A and BRCA1 to learn more information about the genes. In some embodiments, if a caregiver selects one of the genes, the system 102 presents the caregiver with an option to view medical findings associated with the selected gene. Alternatively or additionally, the system 102 may present the user with information related to known variants or genetic defects associated with the medical findings.

Figure 16:
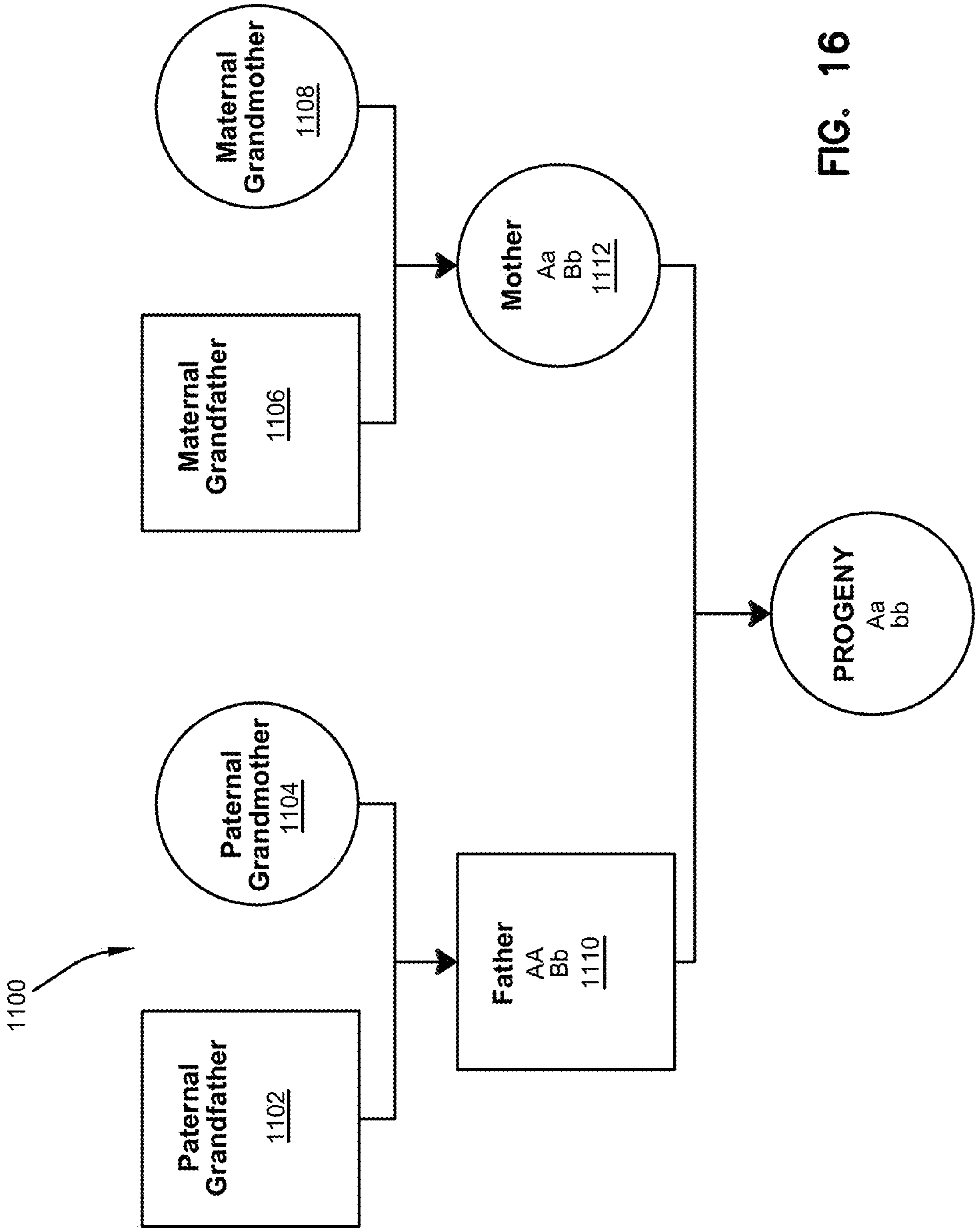
FIG. 16 is yet another exemplary embodiment of an interactive user interface presented by the electronic healthcare system.

FIG. 16 depicts an alternate embodiment of user display 1000 shown in FIG. 15 that functions in the same way as described herein with respect to FIG. 15. In particular, FIG. 16 displays a user display 1100. The display 1100 is useful for predicting lethal or pathogenic variant genes that may be passed from the mother or father to progeny. The display 1100 includes boxes indicative of paternal grandfather history 1102, paternal grandmother history 1104, maternal grandfather history 1106, maternal grandmother history 1108, father history 1110, mother history 1112, and potential genotypes of progeny based on genes carried by the mother and father. In the example, the display 1100 shows the history of dominate gene A and pathogenic recessive gene b. In the example, the father and mother's lineage are carriers of recessive gene b. In the example, the caregiver utilizes the display 1100 to determine the possibility of transfer of genetic defects in the mother or father being passed to offspring. The display 1100 may include a probability that the offspring may suffer from a genetic disorder associated with a specific gene or genes or be a carrier of pathogenic variant gene. As shown in FIG. 16, a progeny of the mother and father has a 25% chance of inheriting double recessive gene b (bb) which would result in a disease state.

Figure 17:
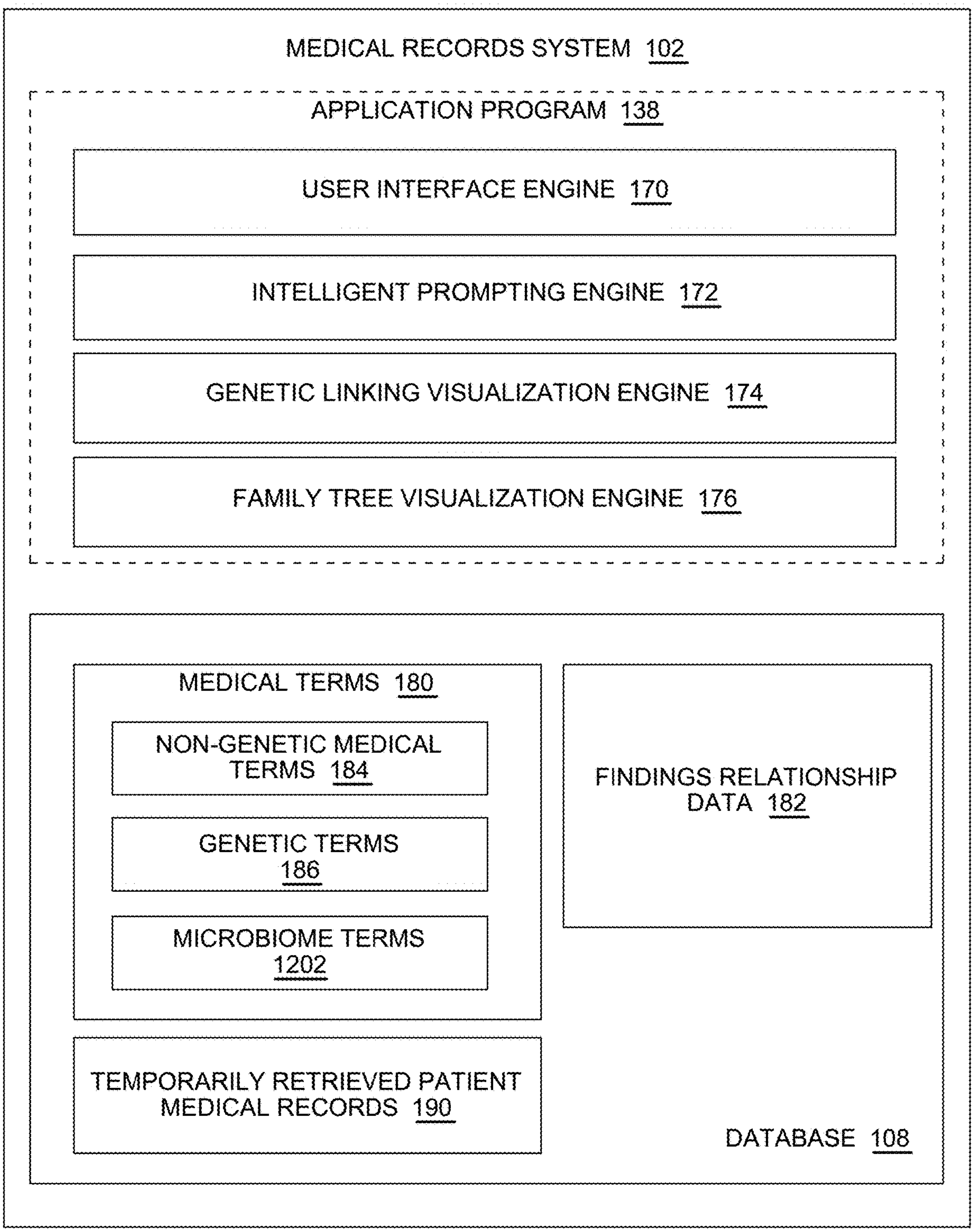
FIG. 17 illustrates an alternate exemplary architecture of an application program of the computing device and a database of the electronic healthcare system.

FIG. 17 illustrates further exemplary aspects of the system 102. More specifically, FIG. 17 depicts an alternate example of the medical information records system 102. The medical information records system 102 functions in the same way as described herein with respect to FIG. 4. However, in the alternate design, the medical terms 180 in the database 108 includes microbiome terms 1202 in addition to the non-genetic medical terms 184 and the genetic terms 186.

The microbiome terms 1202 include medical findings associated with microorganisms within the human microbiome, which can work in conjunction with the human body to provide energy, vitamins, protection, and assistance with digestion. The resident population or equilibrium of the microbiome, disruption of the microbiome, or changes in the resident population of equilibrium of the microbiome due to an injury, pathenogicity, antibiotic use, environmental factors including chemicals, toxins, diet, exercise, and weight gain, or sociodemographic factors including geography, race, culture, and ethnicity, have been associated with health problems in the host human. The microbiome terms 1202 include any medical findings associated with microorganisms within the microbiome that are linked to health problems in human beings including obesity, malnutrition, autism, pre-term labor and delivery, caries, diabetes, multiple sclerosis, atherosclerosis, lymphomas, leukemia, heart disease, endocarditis, asthma, eczema, liver disease, peptic ulcers, non-ulcer dyspepsia, psoriasis, reflux esophagitis, diseases of the intestines including irritable bowel syndrome, colitis, and Crohn's disease, autism, and cancers including colorectal cancer, prostate cancer, uterine cancer, bladder cancer, oral cancer, nasopharyngeal cancer, Kaposi's carcinoma, hepatocellular carcinoma, cholangiocarcinoma, testicular cancer, endometrial carcinoma, and anogenital carcinoma.

Genetic terms included within the microbiome terms 1202 correspond to genes, 16S ribosomal genome sequences, reference genome sequences, or metagenome sequences from the human microbiome, which can include eukaryotes, archaea, bacteria and viruses. These genetic terms can be associated with a particular abnormal medical finding(s) abnormal medical finding(s) or with a particular microorganism or combination of microorganisms of the microbiota and can be used visually represented by the system, as shown for example in FIG. 18, to identify microorganism or genes within the microbiome that may be causative or contributing to the medical condition. Identifying, for example, a particular bacterium, virus, or combination of bacteria in the microbiome of the patient can be useful indicators of a particular health condition or risk factor that the patient may develop a particular health condition. Identifying a particular gene within the microbiota that can exert an effect on or control over genes of the patient can also be an indicator of a health condition or a risk factor that the patient may develop a particular health condition. For example, the microbiome gene may induce expression or overexpression of a particular human gene that results in a cancer. In embodiments, manipulation of the microbiome by drug therapy or seeding of the microbiome with a particular bacterium or combination of bacteria may be used to treat a particular health condition or reduce the risk of the patient developing a particular health condition.

The microbiome terms 1202 can be organized into subbiomes to distinguish the microbiota of one system or area of the body from the microbiota that of another system or area of the body. These sub-biomes include but are not limited to gastrointestinal tract microbiome, urogenital tract microbiome, oral cavity microbiome, naso-pharyngeal tract microbiome, blood microbiome, abdomen microbiome, airway microbiome, eye microbiome, heart microbiome, liver microbiome, lymph node microbiome, tumor microbiome, and wound microbiome. In an embodiment, the microbiome terms 1202 may include cancerbiom terms comprising medical findings associated with the microbiome of different cancer or tumor types.

In some embodiments, the microbiome terms 1202 each include a corresponding medical code used internally by the system 102. In the alternate embodiment of FIG. 17, the findings relationship data 182 includes relationship information linking the microbiome terms 1202 with the other medical terms 180. In some embodiments, the findings relationship data 182 relates medical codes corresponding to each term in the medical terms 180 with one or more other terms in the medical terms 180. The functioning of the findings relationship data 182 is similar to the description herein with respect to FIG. 4; however, in addition to the non-genetic medical terms 184 and the genetic terms 186, which include medical findings genes related to the human body, the findings relationship data 182 further incorporates the microbiome terms 1202, which includes medical findings related to the microorganisms of the microbiome of the human body.

In some embodiments, the genetic linking visualization engine 174 may further utilize the intelligent prompting engine 172 to present a list of related microbiome genes from the microbiome terms 1202. The list of related microbiome genes may be presented in one of several methods. For example, the list may be presented in graphical format depicting the genes and associated microorganisms or locations within associated microorganisms. The listing of microbiome genes may be the same as described above with reference to the human genes and medical findings. For example, the system may display the genes of a bacterium or virus known to cause clinical or medical conditions. The user may, for example, select a microbiome gene, such as a gene of a bacterium or virus, presented on the display to learn more about the particular microbiome gene or associated human health concerns.

Figure 18:
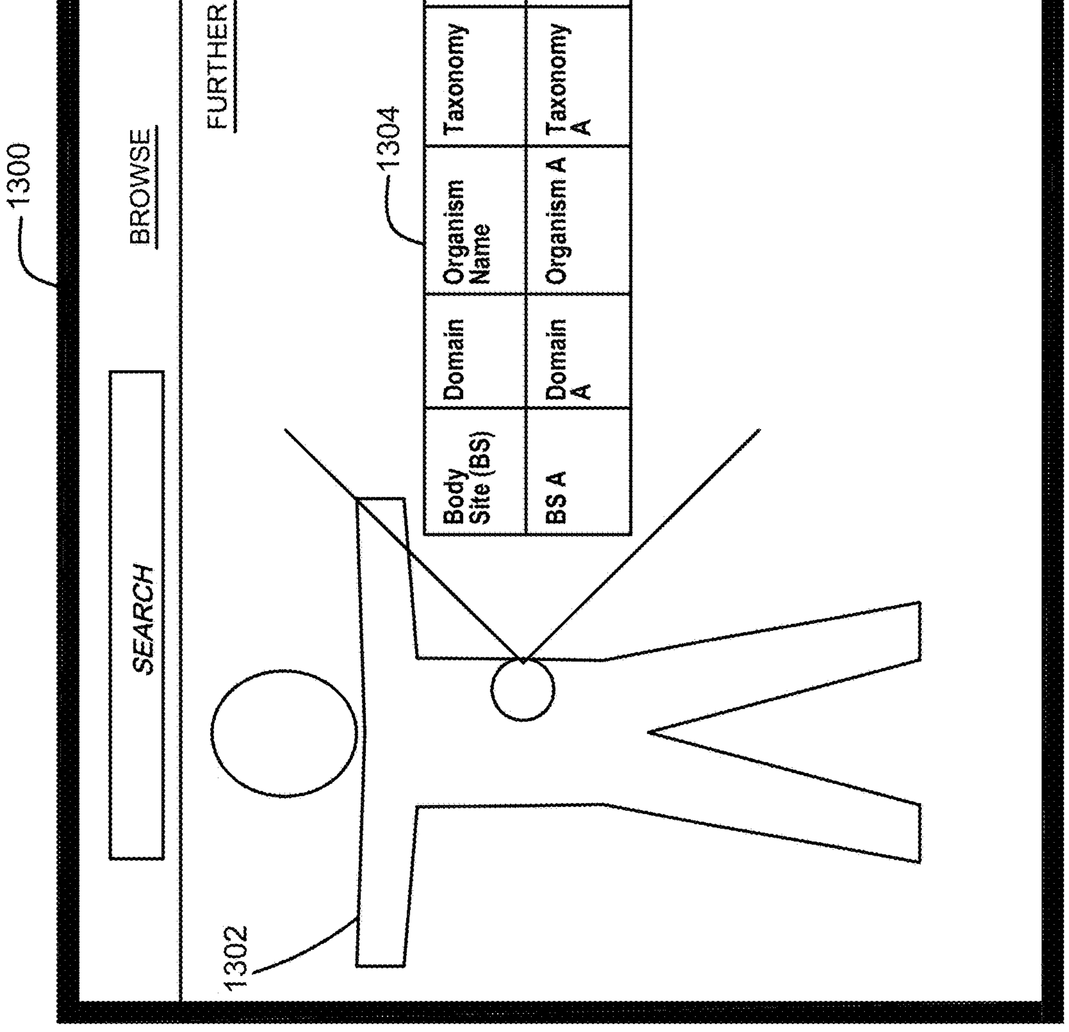
FIG. 18 is yet another exemplary embodiment of an interactive user interface presented by the electronic healthcare system.

Now referring to FIG. 18, an example of a display 1300 including intelligently prompted microbiome information based on an input is shown. The display 1300 includes a human image 1302 and a table 1304.

The human image 1302 indicates the body site of the microbiome related to the input. In particular, a body site may include gastrointestinal tract, urogenital tract, oral cavity, naso-pharyngeal tract, blood, abdomen, airways, eye, heart, liver, lymph node, and the like. The table 1304 includes specific information relating to the microbiome and the organisms composing the microbiome of the selected body site. In particular, the table 1304 includes further information such as the domain, organism(s) name, taxonomy, related disease information, and internal information, such as, a relevance score and an internal medical code. In the example, domain includes archaeal, bacterial, virus, and eukaryal. The taxonomy can include species name, strain and classification information, phenotype characteristics, prevalence and source, medical findings, medical decisions support, treatments, genetic information, testing protocols, and references as described herein and illustrated in FIGS. 5 and 14. The disease classes can include aging, cancer, cardiovascular, chemical dependency, developmental, hematological, immune, infection, metabolic, mitochondrial, neurologic, normal variation, other, pharmacogenomic, psychiatric, renal, reproduction, vision, and unknown. The disease terms include medical terminology descriptive of the disease class, phenotype of disease, or the microorganism of interest.

Figure 19:
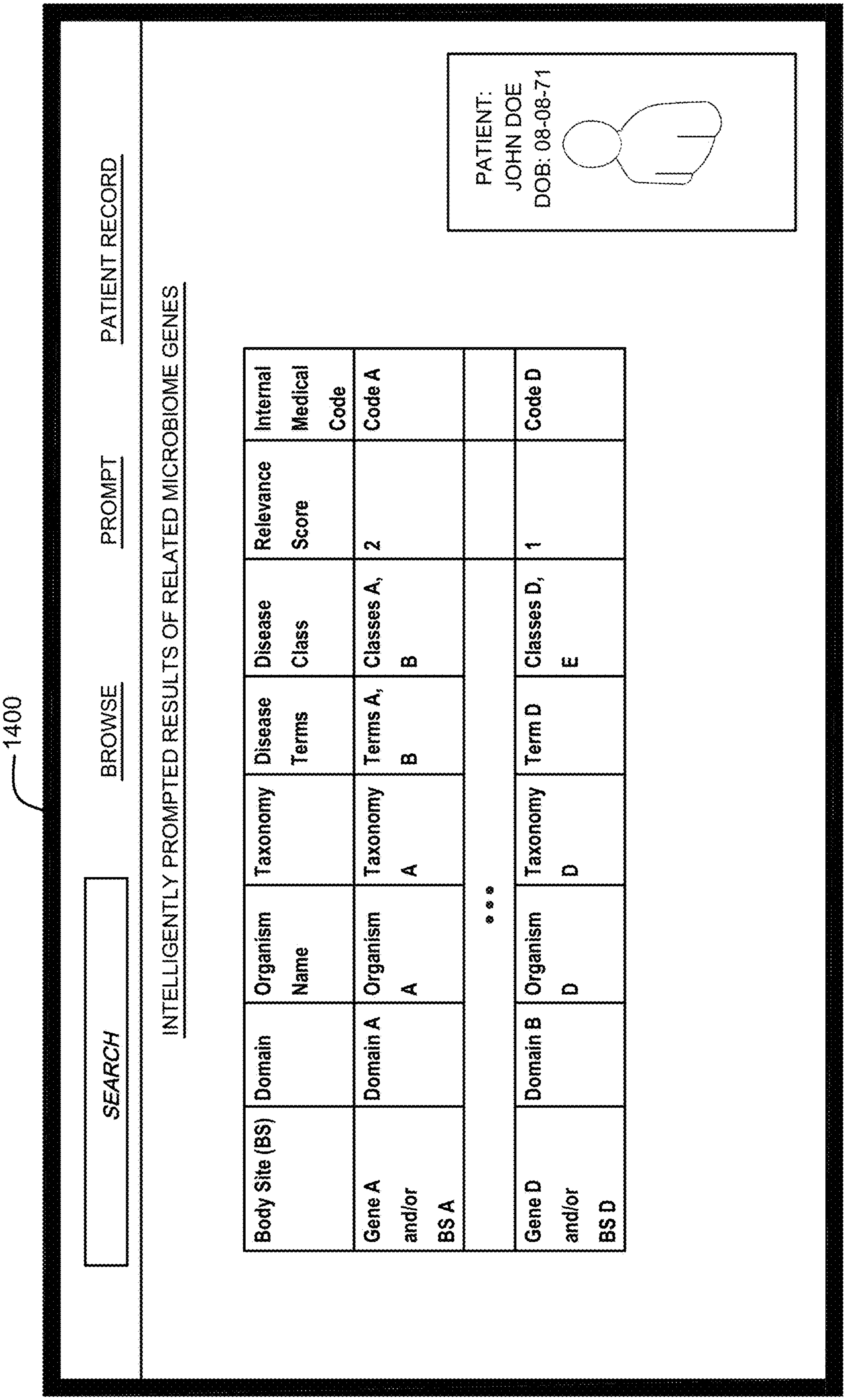
FIG. 19 is yet another exemplary embodiment of an interactive user interface presented by the electronic healthcare system.

FIG. 19 depicts a user display 1400. The display 1400 is an example of a user display that is presented to the user upon clicking the table 1304. In other embodiments, the display 1400 is presented to the user instead of the display 1300. In other words, the display 1400 is presented to the user as an intelligent prompt result. In particular, the display 1400 includes a table that is similar to the table 1304 and includes the same or similar information. It is understood that the table may include more or less information than what is shown in FIG. 18. Further, as with other tables presented herein, each item in the table 1304 may be selectable for further information as described above with reference to other displays.

FIG. 20 depicts a user display 1500. In particular, the display 1500 is an example of what is presented to a user upon selecting a particular microbiome gene displayed on one of the displays 1300, 1400. The display 1500 includes information in a list 1502. As with the other lists described herein, the list 1502 may be selectively expandable.

The list 1502 includes a variety of information related to the selected microbiome gene. In particular, the list 1502 can include species name, strain and classification information, phenotype characteristics, prevalence and source, medical findings, medical decisions support, treatments, genetic information, testing protocols, and references as described herein with respect to FIGS. 5 and 14.

Figure 21:
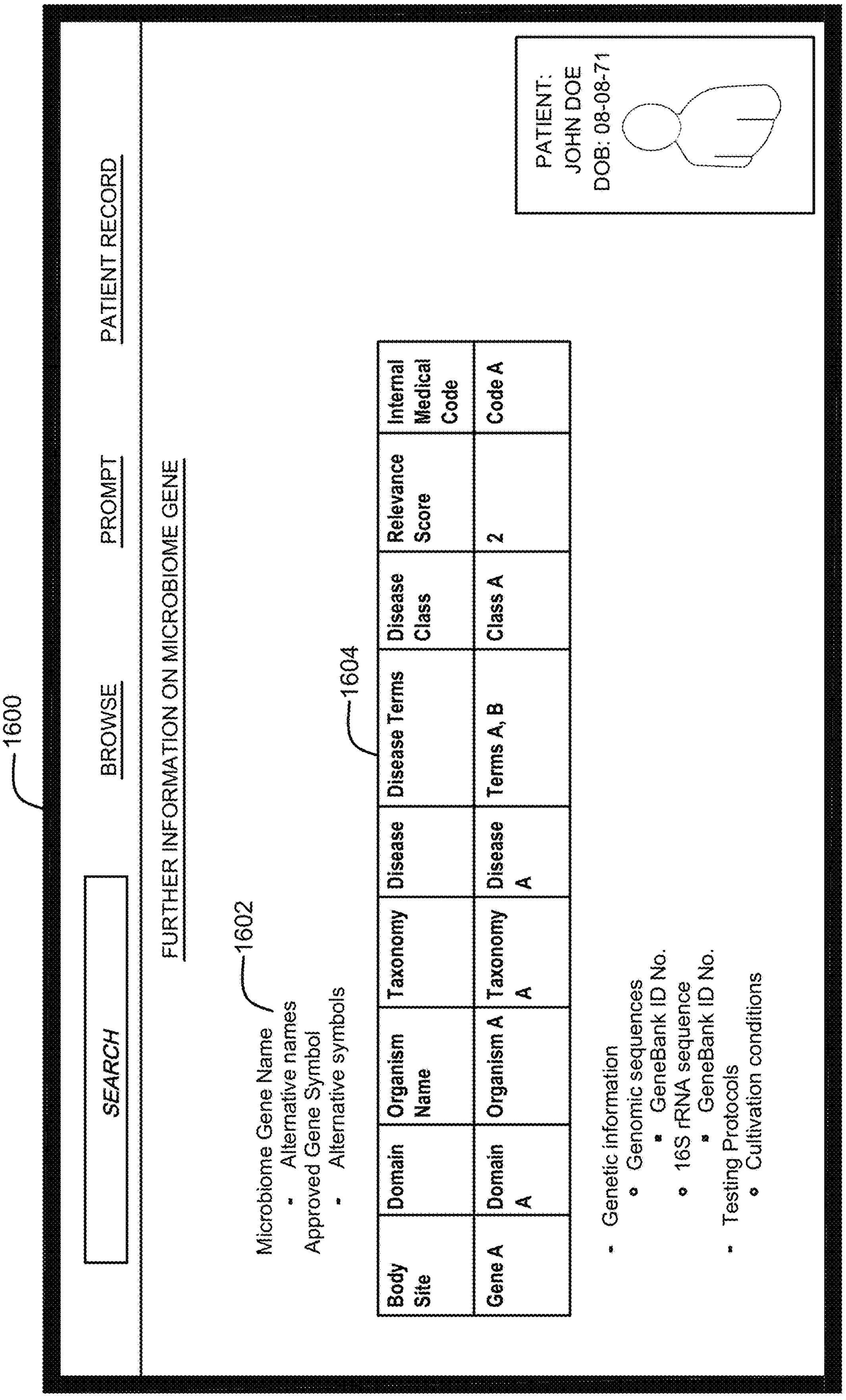
FIG. 21 is yet another exemplary embodiment of an interactive user interface presented by the electronic healthcare system.

Now referring to FIG. 21, an example display 1600 is shown. The display 1600 is an example of what is presented to a user upon selecting a particular microbiome gene displayed on one of the displays 1300-1500. The display 1600 includes a list 1602, which may be selectively expandable as described above. The list 1602 includes a table 1604 which includes particular information on the microbiome gene selected.

The list 1602 and the table 1604 generally present information about the characteristics of the selected microbiome gene. For example, the microorganism(s) comprising the gene, disease, disease terms, and disease classes associated with the gene, taxonomy information associated with the gene or microorganism comprising the gene including genetic information such as gene sequence and genomic sequences associated with the microorganism including GenBank ID numbers and 16S rRNA sequences, and testing protocols for identifying the gene or a microorganism carrying the gene.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:

1. A method comprising:

generating, by a processor, a graphical user interface, the graphical user interface displaying a genetic variant comprising a chromosome, the identity of a gene, and a location of the gene within the chromosome, the graphical user interface comprising a selectable link to further information related to the displayed genetic variant;

presenting, on a display, the genetic variant in a graphical format using a computing device; and upon selecting the selectable link:

retrieving data related to the gene; and modifying the graphical user interface to present the further information related to the displayed genetic variant.

2. The method of claim 1 wherein the selectable link connects the displayed genetic variant to a non-genetic internal medical code, the method further comprising:

determining a relevance score associated with the internal medical code and each of the genetic variants;

filtering the genetic variants based on the relevance score; and presenting a filtered group of the genetic variants in a graphical format using the computing device.

3. The method of claim 1, wherein the graphical format displays one or more genes associated with the genetic variants and locations of the one or more genes on associated chromosomes.

4. The method of claim 3, wherein a user is enabled to select the one or more genes to view more information about the one or more genes.

5. A method comprising:

determining, by a processor, a non-genetic internal medical code associated with genetic information, the non-genetic internal medical code being machine readable;

generating, by a processor, a graphical user interface, the graphical user interface displaying the genetic information, the graphical user interface comprising a selectable link associated with the non-genetic internal medical code and the displayed genetic information; and upon selecting the selectable control:

retrieving data related to medical findings, the medical finding being associated with the genetic information and the non-genetic internal medical code; and presenting the medical findings on a display.

6. The method of claim 5, further comprising:

determining a relevance score associated with the internal medical code and each of the medical findings;

filtering the medical findings based on the relevance score; and presenting a filtered group of the medical findings in a list format using the computing device.

7. The method of claim 5, wherein the list format enables a user to select one of the medical findings to view information about a selected medical finding.

8. The method of claim 7, wherein the information includes whether a patient medical record includes an instance of the selected medical finding.

9. A method comprising:

determining, by a processor, an internal medical code associated with the input, the internal medical code being a non-genetic code;

determining, by a processor, microbiome genetic information associated with the internal medical code, wherein the microbiome genetic information is associated with genes of microorganisms living within a person which are related to the input, the determined microbiome being identified from a first database;

generating, by a processor, a graphical user interface, the graphical user interface displaying the microbiome genetic information, the graphical user interface comprising a selectable link connecting the input to the determined medical findings; and upon selecting the selectable link, presenting the microbiome genetic information in a graphical format using a computing device upon actuating the selectable link, the internal medical code being machine readable and independent of the genetic information.

10. The method of claim 9, wherein the graphical format indicates a microorganism associated with the microbiome genetic information.

11. The method of claim 9, wherein the microbiome genetic information indicates the presence or absence of a microorganism.

12. The method of claim 9 further comprising:

receiving a human genetic variant;

determining an internal medical code associated with the human genetic variant;

determining medical items associated with the internal medical code; and presenting the medical items in a list format on the computing device, wherein the input is at least one of the medical items.

13. A method comprising:

generating, by a processor, a graphical user interface, the graphical user interface displaying a genetic variant comprising a chromosome, the identity of a gene, and a location of the gene within the chromosome; and generating, by the processor, a selectable link connecting the displayed genetic variant to a non-genetic internal medical code, the non-genetic internal medical code associated with further information related to the displayed genetic variant.

14. A system comprising:

a database encoded on a memory device, the database having genetic information associated with abnormal medical findings including a chromosome, the identity of a gene, and the location of the gene within the chromosome; and a computing device in data communication with the database, wherein the computing device programmed to:

generate a graphical user interface displaying the genetic variant;

generating a selectable link, the selectable linking associated with data related to the gene; and display the information related to the gene upon selecting the selectable link.

15. A system comprising:

a database encoded on a memory device, the database having a non-genetic internal medical code associated with genetic information, the non-genetic internal medical code being machine readable; and a computing device in data communication with the database, wherein the computing device programmed to:

generate a graphical user interface displaying the genetic information;

generate a selectable link associated with the displayed genetic information; and upon selecting the selectable control, retrieve data related to medical findings, the medical finding being associated with the genetic information and the non-genetic internal medical code.

* * * * *